(12) United States Patent
Kolczewski et al.

(10) Patent No.: US 7,994,324 B2
(45) Date of Patent: *Aug. 9, 2011

(54) 2-AMINOQUINOLINE DERIVATIVES

(75) Inventors: Sabine Kolczewski, Loerrach (DE); Claus Riemer, Freiburg (DE); Olivier Roche, Folgensbourg (FR); Lucinda Steward, Basel (CH); Juergen Wichmann, Steinen (DE); Thomas Woltering, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 38 days.

This patent is subject to a terminal disclaimer.

(21) Appl. No.: 12/394,092

(22) Filed: Feb. 27, 2009

(65) Prior Publication Data
US 2009/0227584 A1 Sep. 10, 2009

(30) Foreign Application Priority Data

Mar. 7, 2008 (EP) .................................... 08152421

(51) Int. Cl.
*C07D 215/38* (2006.01)
(52) U.S. Cl. ........................ 546/159; 546/160
(58) Field of Classification Search .................. 546/159, 546/160
See application file for complete search history.

(56) References Cited

U.S. PATENT DOCUMENTS

| 2007/0202924 A1* | 8/2007 | Lai et al. ....................... 455/566 |
| 2007/0299074 A1 | 12/2007 | Netz et al. |
| 2008/0146567 A1* | 6/2008 | Kolczewski et al. ....... 514/235.2 |
| 2009/0227628 A1* | 9/2009 | Kolczewski et al. .......... 514/313 |

FOREIGN PATENT DOCUMENTS

| WO | 0187845 | 11/2001 |
| WO | 03037872 | 5/2003 |
| WO | WO 03/080579 | 10/2003 |
| WO | WO 2004/034985 | 4/2004 |
| WO | WO 2004/080463 | 9/2004 |
| WO | WO 2004/096771 | 11/2004 |
| WO | 2004106305 | 12/2004 |
| WO | WO 2005/082871 | 9/2005 |
| WO | 2006103511 | 10/2006 |
| WO | 2008037626 | 4/2008 |
| WO | WO 2008/068157 | 6/2008 |

OTHER PUBLICATIONS

Giordanetto, Bioorg & Med Chem Lett, vol. 17, pp. 4232-4241, 2007.*
Hoyer et al., Pharmacol. Rev. vol. 46, pp. 157-204 (1994).
Rees et al., FEBS Lett. vol. 355, pp. 242-246 (1994).
Francken et al., Eur. J. Pharmacol. vol. 361, pp. 299-309 (1998).
Noda et al., J. Neurochem. vol. 84, pp. 222-232 (2003).
Thomas, D. R., Pharmacol. Ther. vol. 111(3) pp. 707-714 (2006).
Doly et al., The Journal of Comparative Neurology vol. 476 pp. 316-329 (2004).
Dubertret et al., J. of Psychiatric Research vol. 35 pp. 371-376 (2004).
Garcia-Ladona et al., 36th Annual Meeting Soc. Neurosci. Oct. 14-Oct. 18, Atlanta Abstract 33.1 (2006).
Drescher et al., 36th Annual Meeting Soc. Neurosci. Oct. 14-Oct. 18, Atlanta Abstract 33.2 (2006).
Thomas, Neuropharmacology vol. 51(3) pp. 566-577 (2006).
Barnes et al., Neuropharmacology vol. 38 pp. 1083-1152 (1999).
Pasqualetti et al., Mol. Brain Res. vol. 56 pp. 1-8 (1998).
Wang et al., Neurosci. Lett. vol. 278 pp. 9-12 (2000).
Birkett et al., Neuroreport vol. 11 pp. 2017-2020 (2000).
Iwata et al., Mol. Psychiatry vol. 6 pp. 217-219 (2001).
Duncan et al., Brain Research vol. 869, pp. 178-185 (2000).
Sprouse et al., Synapse, vol. 54(2) pp. 111-118 (2004).
Office Action issued Jul. 1, 2010 in corresponding U.S. Appl. No. 11/946,947, filed Nov. 29, 2007.
Office Action issued Jul. 1, 2010 in corresponding U.S. Appl. No. 12/394,083, filed Feb. 27, 2009.
Office Action issued Aug. 10, 2010 in corresponding U.S. Appl. No. 12/394,083, filed Feb. 27, 2009.
Burkhalter, XP002469319 pp. 4837-4839 (1951).
Database CA Chem. Abstract XP002542080.
Acheson, J. Chem. Soc. pp. 4440-4443 (1955).

* cited by examiner

*Primary Examiner* — D Seaman
(74) *Attorney, Agent, or Firm* — George W. Johnston; Patricia S. Rocha-Tramaloni; Kimberly J. Prior

(57) ABSTRACT

The present invention is concerned with 2-aminoquinoline derivatives, in particular compounds of formula (I)

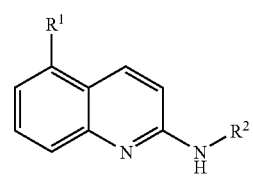

I wherein $R^1$ and $R^2$ are as described herein, pharmaceutical compositions containing such compounds, and methods for their manufacture. The compounds of the invention are 5-HT$_{5A}$ receptor antagonists useful in the prevention and/or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, abuse of drugs, motor disorders such as Parkinson's disease, psychiatric disorders or gastrointestinal disorders.

28 Claims, No Drawings

2-AMINOQUINOLINE DERIVATIVES

PRIORITY TO RELATED APPLICATION(S)

This application claims the benefit of European Patent Application No. 08152421.7, filed Mar. 7, 2008, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor ($5-HT_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human $5-HT_{5A}$ serotonin receptor has been described in *FEBS Letters*, 355, 242-246 (1994). The sequence is not closely related to that of any previously known serotonin receptor, with the best homology being 35% to the human $5-HT_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the $5-HT_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The *Pharmacology & Therapeutics*, 111, 707-714 (2006) describes potential therapeutic utility of $5-HT_{5A}$ receptor ligands for the treatment of circadian rhythm, sleep disturbances, mood disorders, schizophrenia, cognitive disorders and autism. The *Journal of Comparative Neurology*, 476, 316-329 (2004) suggests based on the localisation pattern of the $5-HT_{5A}$ receptor in the rat spinal cord that $5-HT_{5A}$ receptors may play a role in central motor control, nociception and autonomic function such as stress induced urinary incontinence and overactive bladder. The *Journal of Psychiatric Research*, 38, 371-376 (2004) describes evidence for a potential significant role of the $5-HT_{5A}$ gene in schizophrenia and more specifically in patients with later age at onset.

SUMMARY OF THE INVENTION

The present invention provides 2-aminoquinoline derivatives. In particular, the present invention provides compounds of formula (I)

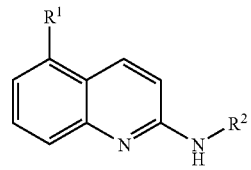

I wherein
wherein
$R^1$ is alkyl, aminoalkyl, hydroxyalkyl, haloalkyl, cyanoalkyl, cycloalkyl, —C(=N—$R^i$)$NR^{ii}R^{iii}$, —C(=N—$R^i$)-cycloalkyl, —C(=N—$R^i$)-alkyl, —C(O)-cycloalkyl, —C(O)alkyl, heterocycloalkyl, —O-alkyl, —O-alkylene-O-alkyl, —O-alkylene-S(O)$_x$-alkyl, or —$NR^aR^b$;
$R^a$ and $R^b$ are each independently H, alkyl, cycloalkyl, -alkylene-S(O)$_x$-alkyl, —S(O)$_2NR^{iv}R^v$, —S(O)$_2$-alkyl, —S(O)$_2$-cycloalkyl, —C(O)-cycloalkyl, —C(O)alkyl, —C(O)-alkylene-heterocycloalkyl, —C(O)-heterocycloalkyl, —C(O)$NR^{vi}R^{vii}$, —C(O)-alkylene-$NR^{viii}R^{ix}$, —C(O)-alkylene-O-alkyl, -alkylene-$NR^{viii}R^{ix}$, -alkylene-O-alkyl, -alkylene-cycloalkyl, heterocycloalkyl, —C(O)—CH$_2$-phenyl, —C(O)—CH$_2$-heteroaryl;
$R^i$, $R^{ii}$, and $R^{iii}$ are each independently OH, alkoxy or H;
$R^{iv}$, $R^v$, $R^{vi}$, $R^{vii}$, $R^{viii}$ and $R^{ix}$ are each independently H, alkyl, cycloalkyl or -alkylene-N(alkyl)$_2$;
x is 0, 1 or 2, and
$R^2$ is 5- or 6-membered cycloalkyl or heterocycloalkyl, anellated with a benzo ring, wherein the benzo moiety is unsubtituted or substituted with one, two or three alkoxy, halo, alkyl or haloalkyl; and wherein
heterocycloalkyl is unsubstituted or substituted with one or more oxo, alkyl, halo, haloalkyl, haloalkoxy, alkoxy, hydroxy, hydroxyalkyl, or CN; and
phenyl and heteroaryl are each independently unsubstituted or substituted with one or more halo, alkoxy, haloalkyl, alkyl, haloalkoxy, hydroxy, or CN;
or a pharmaceutically acceptable salt thereof.

The compounds of formula I can contain asymmetric carbon atoms. Accordingly, the present invention includes all stereoisomeric forms of the compounds of formula I, including each of the individual enantiomers and mixtures thereof, i.e. their individual optical isomers and mixtures thereof.

The present invention also provides pharmaceutical compositions containing a compound of formula I or a pharmaceutically acceptable salt thereof and a pharmaceutically acceptable carrier. The invention further provides methods for the manufacture of the compounds and compositions of the invention.

Compounds of formula I have good activity on the $5-HT_{5A}$ receptor. Therefore, the invention provides compounds of formula I or pharmaceutically acceptable salts thereof as well as their use in the manufacture of medicaments for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders), psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, nicotine, benzodiazepines, alcohol (ethanol), caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "alkyl" denotes monovalent linear or branched saturated hydrocarbon moiety, consisting solely of carbon and hydrogen atoms, having from 1 to 7 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms.

As used herein, the term "alkylene" means a linear saturated divalent hydrocarbon radical of one to seven carbon atoms or a branched saturated divalent hydrocarbon radical of three to seven carbon atoms. Preferred are divalent hydrocarbon radicals of one to four carbon atoms. In case alkylene is located in between two heteroatoms, it is preferably from 2 to 7 carbon atoms, more preferably from 2 to 4 carbon atoms.

The term "halo" denotes chloro, iodo, fluoro and bromo. Preferred halo are fluoro, chloro and bromo, more preferred are fluoro and chloro.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include but are not limited to methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, trifluoromethyl.

The term "hydroxyalkyl" denotes an alkyl group as defined above wherein at least one of the hydrogen atoms of the alkyl group is replaced by a hydroxy group. Examples of hydroxyalkyl include but are not limited to methyl, ethyl, propyl, isopropyl, isobutyl, sec-butyl, tert-butyl, pentyl or n-hexyl wherein one or more hydrogen atoms are replaced by OH, as well as those hydroxyalkyl groups specifically illustrated by the examples herein below.

The term "cyanoyalkyl" denotes an alkyl group as defined above wherein at least one of the hydrogen atoms of the alkyl group is replaced by a cyano group. Examples of cyanoalkyl include but are not limited to methyl, ethyl, propyl, isopropyl, isobutyl, sec-butyl, tert-butyl, pentyl or n-hexyl wherein one or more hydrogen atoms are replaced by CN, as well as those cyanoalkyl groups specifically illustrated by the examples herein below.

The term "aminoyalkyl" denotes an alkyl group as defined above wherein at least one of the hydrogen atoms of the alkyl group is replaced by a amino group, i.e. a —NH$_2$ group. Examples of aminoalkyl include but are not limited to methyl, ethyl, propyl, isopropyl, isobutyl, sec-butyl, tert-butyl, pentyl or n-hexyl wherein one or more hydrogen atoms are replaced by —NH$_2$, as well as those groups specifically illustrated by the examples herein below.

The term "alkoxy" denotes a group —O—R' wherein R' is alkyl as defined above.

The term "anellated", "annellated", "annulated", "fused" or "condensed" denotes the attachment of a further ring to an existing ring via a common single or double bond, i.e. both rings share one single or double bond. Annular residues are hence constructed from side-on condensed cyclic segments.

The term "aromatic" means the presence of an electron sextet in a ring, according to Hückel's rule.

The term "cycloalkyl" refers to a monovalent saturated monocyclic hydrocarbon radical of 3 to 7 ring carbon atoms, such as cyclopropyl, cyclobutanyl, cyclopentyl, cyclohexyl or cycloheptyl. Preferred are cyclopropyl, cyclopentyl and cyclohexyl. Cycloalkyl is optionally substituted as described herein.

The term "heterocycloalkyl" refers to a monovalent saturated 5- to 6-membered monocyclic ring system containing one, two or three ring heteroatoms selected from N, O and S, the remaining ring atoms being carbon atoms. "Heterocycloalkyl" can be unsubstituted or substituted as described herein. Examples of heterocycloalkyl moieties include, but are not limited to pyrrolidinyl, tetrahydrothiophenyl, tetrahydropyranyl, tetrahydrothiopyranyl, piperidinyl, piperazinyl, morpholinyl, or thiomorpholinyl. Preferred examples are tetrahydrothiophenyl, tetrahydropyranyl, piperidinyl, piperazinyl or morpholinyl. Examples for substituents on heterocycloalkyl include, but are not limited to oxo, alkyl, halo, haloalkyl, haloalkoxy, alkoxy, hydroxy, hydroxyalkyl, or CN. Preferred substituents are oxo or alkyl.

The term "heteroaryl" as defined herein denotes a monocyclic monovalent aromatic ring of 5 or 6 ring atoms containing one, two, or three ring heteroatoms selected from N, O, and S, the remaining ring atoms being C. Examples of heteroaryl moieties include, but are not limited to thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl, or pyridazinyl. Preferred examples for heteroaryl are thiophenyl and imidazolyl. The heteroaryl ring is optionally substituted as defined herein. Examples for substituents on aromatic ring systems disclosed herein, and in particular on heteroaryl and on phenyl include, but are not limited to halo, alkoxy, haloalkyl, alkyl, haloalkoxy, hydroxy, or CN. Preferred substituents are halo or alkoxy.

As used herein, the term "thiophenyl" is synonymous with "thienyl" and each represents a thiophene substituent, i.e., $C_4H_4S$.

When indicating the number of subsituents, the term "one or more" means from one substituent to the highest possible number of substitution, i.e. replacement of one hydrogen up to replacement of all hydrogens by substituents. Thereby, one, two or three substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In detail, the present invention relates to compounds of the general formula (I)

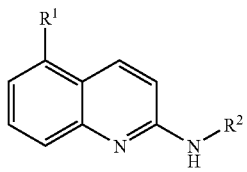

I wherein $R^1$ is alkyl, aminoalkyl, hydroxyalkyl, haloalkyl, cyanoalkyl, cycloalkyl, —C(=N—$R^i$)N$R^{ii}R^{iii}$, —C(=N—$R^i$)-cycloalkyl, —C(=N—$R^i$)-alkyl, —C(O)-cycloalkyl, —C(O)alkyl, heterocycloalkyl, —O-alkyl, —O-alkylene-O-alkyl, —O-alkylene-S(O)$_x$-alkyl, or —N$R^aR^b$;

$R^a$ and $R^b$ are each independently H, alkyl, cycloalkyl, -alkylene-S(O)$_x$-alkyl, —S(O)$_2$N$R^{iv}R^v$, —S(O)$_2$-alkyl, —S(O)$_2$ -cycloalkyl, —C(O)-cycloalkyl, —C(O)alkyl, —C(O)-alkylene-heterocycloalkyl, —C(O)-heterocycloalkyl, —C(O)N$R^{vi}R^{vii}$, —C(O)-alkylene-N$R^{viii}R^{ix}$, —C(O)-alkylene-O-alkyl, -alkylene-N$R^{viii}R^{ix}$, -alkylene-O-alkyl, -alkylene-cycloalkyl, heterocycloalkyl, —C(O)—CH$_2$-phenyl, —C(O)—CH$_2$-heteroaryl;

$R^i$, $R^{ii}$, and $R^{iii}$ are each independently OH, alkoxy or H;

$R^{iv}$, $R^v$, $R^{vi}$, $R^{vii}$, $R^{viii}$ and $R^{ix}$ are each independently H, alkyl, cycloalkyl or -alkylene-N(alkyl)$_2$;

x is 0, 1 or 2, and $R^2$ is 5- or 6-membered cycloalkyl or heterocycloalkyl, anellated with a benzo ring, wherein the benzo moiety is unsubtituted or substituted with one, two or three alkoxy, halo, alkyl or haloalkyl; and wherein heterocycloalkyl is unsubstituted or substituted with one or more oxo, alkyl, halo, haloalkyl, haloalkoxy, alkoxy, hydroxy, hydroxyalkyl, or CN; and phenyl and heteroaryl are each independently unsubstituted or substituted with one or more halo, alkoxy, haloalkyl, alkyl, haloalkoxy, hydroxy, or CN;

or a pharmaceutically acceptable salt thereof.

The term "5- or 6-membered cycloalkyl or heterocycloalkyl, anellated with a benzo ring" means that the attachment to the 2-aminoquinoline derivative is on the 5- or 6-membered cycloalkyl or heterocycloalkyl ring, such as shown in formula G:

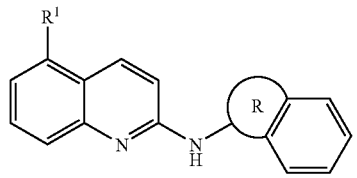

(G)

wherein R denotes the 5- or 6-membered cycloalkyl or heterocycloalkyl ring.

In certain embodiments, $R^1$ is as defined above.

In certain embodiments, $R^1$ is alkyl, aminoalkyl, hydroxyalkyl, haloalkyl, cyanoalkyl, or cycloalkyl; preferably, $R^1$ is alkyl, aminoalkyl or cycloalkyl.

In certain embodiments, $R^1$ is —C(=N—$R^i$)N$R^{ii}R^{iii}$, —C(=N—$R^i$)-cycloalkyl, or —C(=N—$R^i$)-alkyl; preferably, $R^1$ is —C(=N—$R^i$)N$R^{ii}R^{iii}$, or —C(=N—$R^i$)-cycloalkyl. Thereby, $R^i$, $R^{ii}$ and $R^{iii}$ are each independently OH, alkoxy or H. Preferably, $R^i$, $R^{ii}$ and $R^{iii}$ are each independently H or OH.

In certain embodiments, $R^1$ is —C(O)-cycloalkyl, or —C(O)alkyl, preferably —C(O)-cycloalkyl.

In certain embodiments, $R^1$ is heterocycloalkyl, wherein heterocycloalkyl is as defined above and is unsubstituted or substituted as defined above. As an example, heterocycloalkyl is morpholin-4-yl.

In certain embodiments, $R^1$ is —O-alkyl, —O-alkylene-O-alkyl, or —O-alkylene-S(O)$_x$-alkyl, wherein x is 0, 1 or 2.

In certain embodiments, $R^1$ is —N$R^aR^b$, wherein $R^a$ and $R^b$ are each independently H, alkyl, cycloalkyl, -alkylene-S(O)$_x$-alkyl, —S(O)$_2$N$R^{iv}R^v$, —S(O)$_2$-alkyl, —S(O)$_2$ -cycloalkyl, —C(O)-cycloalkyl, —C(O)alkyl, —C(O)-alkylene-heterocycloalkyl, —C(O)-heterocycloalkyl, —C(O)N$R^{vi}R^{vii}$, —C(O)-alkylene-N$R^{viii}R^{ix}$, —C(O)-alkylene-O-alkyl, -alkylene-N$R^{viii}R^{ix}$, -alkylene-O-alkyl, -alkylene-cycloalkyl, heterocycloalkyl, —C(O)—CH$_2$-phenyl, —C(O)—CH$_2$-heteroaryl;

$R^{iv}$, $R^v$, $R^{vi}$, $R^{vii}$, $R^{viii}$ and $R^{ix}$, are each independently H, alkyl, cycloalkyl or -alkylene-N(alkyl)$_2$; and x is 0, 1 or 2.

It is to be understood that heterocycloalkyl is as defined above, and is unsubstituted or substituted as defined above. Phenyl and heteroaryl are as defined above, and are unsubstituted or substituted as defined above.

In certain embodiments, $R^1$ is —N$R^aR^b$, wherein $R^a$ and $R^b$ are each independently H, alkyl, -alkylene-S(O)$_x$-alkyl, —S(O)$_2$N$R^{iv}R^v$, —S(O)$_2$-alkyl, —S(O)$_2$-cycloalkyl, —C(O)-cycloalkyl, —C(O)alkyl, —C(O)-alkylene-heterocycloalkyl, —C(O)-heterocycloalkyl, —C(O)-alkylene-N$R^{viii}R^{ix}$, —C(O)-alkylene-O-alkyl, -alkylene-N$R^{viii}R^{ix}$, -alkylene-cycloalkyl, heterocycloalkyl, —C(O)—CH$_2$-phenyl, or —C(O)—CH$_2$-heteroaryl;

$R^{iv}$, $R^v$, $R^{viii}$ and $R^{ix}$ are each independently H, alkyl, cycloalkyl or -alkylene-N(alkyl)$_2$; and x is 0, 1 or 2.

It is to be understood that heterocycloalkyl is as defined above, and is unsubstituted or substituted as defined above. Phenyl and heteroaryl are as defined above, and are unsubstituted or substituted as defined above.

In certain embodiments, $R^1$ is —N$R^aR^b$, wherein $R^a$ and $R^b$ are each independently H, alkyl, -alkylene-S(O)$_x$-alkyl, —S(O)$_2$N(alkyl)$_2$, —S(O)$_2$ -alkyl, —S(O)$_2$-cycloalkyl, —C(O)-cycloalkyl, —C(O)alkyl, —C(O)—CH$_2$-(4-methyl-piperazin-1-yl), —C(O)—CH$_2$-(morpholin-4-yl), —C(O)—

CH$_2$-(tetrahydropyran-4-yl), —C(O)(4-methyl-piperazin-1-yl), —C(O)(1-methyl-piperidin-4-yl), —C(O)-alkylene-N(alkyl)$_2$, —C(O)-alkylene-O-alkyl, -alkylene-N(alkyl)$_2$, -alkylene-cycloalkyl, 1,1-dioxo-tetrahydrothiophen-3-yl, tetrahydropyran-4-yl, —C(O)—CH$_2$-phenyl, —C(O)—CH$_2$-(thiophen-2-yl), —C(O)—CH$_2$-(imidazol-1-yl), and x is 0, 1 or 2; and wherein phenyl is unsubstituted or substituted by one or two fluoro, chloro or alkoxy.

In certain embodiments,

R$^1$ is alkyl, aminoalkyl, cycloalkyl, —C(=N—OH)NH$_2$, —C(=N—OH)-cycloalkyl, —C(O)-cycloalkyl, heterocycloalkyl, —O-alkyl, —O-alkylene-O-alkyl, —O-alkylene-S(O)$_x$-alkyl, or —NR$^a$R$^b$;

R$^a$ and R$^b$ are each independently H, alkyl, -alkylene-S(O)$_x$-alkyl, —S(O)$_2$NR$^{iv}$R$^v$, —S(O)$_2$-cycloalkyl, —C(O)-cycloalkyl, —C(O)-alkylene-heterocycloalkyl, —C(O)-heterocycloalkyl, —C(O)-alkylene-NR$^{viii}$R$^{ix}$, —C(O)-alkylene-O-alkyl, -alkylene-NR$^{viii}$R$^{ix}$, -alkylene-cycloalkyl, heterocycloalkyl, —C(O)—CH$_2$-phenyl, —C(O)—CH$_2$-heteroaryl;

R$^{iv}$, R$^v$, R$^{viii}$ and R$^{ix}$ are each independently H, alkyl, cycloalkyl or -alkylene-N(alkyl)$_2$; and x is 0, 1 or 2.

It is to be understood that heterocycloalkyl is as defined above, and is unsubstituted or substituted as defined above. Phenyl and heteroaryl are as defined above, and are unsubstituted or substituted as defined above.

In certain embodiments,

R$^1$ is alkyl, aminoalkyl, cycloalkyl, —C(=N—R$^i$)NR$^{ii}$R$^{iii}$, —C(=N—R$^i$)-cycloalkyl, —C(O)-cycloalkyl, heterocycloalkyl, —O-alkyl, —O-alkylene-O-alkyl, —O-alkylene-S(O)$_x$-alkyl, or —NR$^a$R$^b$;

R$^a$ and R$^b$ are each independently H, alkyl, -alkylene-S(O)$_x$-alkyl, —S(O)$_2$NR$^{iv}$R$^v$, —S(O)$_2$-cycloalkyl, —C(O)-cycloalkyl, —C(O)-alkylene-heterocycloalkyl, —C(O)-heterocycloalkyl, —C(O)-alkylene-NR$^{viii}$R$^{ix}$, —C(O)-alkylene-O-alkyl, -alkylene-NR$^{viii}$R$^{ix}$, -alkylene-cycloalkyl, or heterocycloalkyl;

R$^i$ is OH;

R$^i$, R$^{ii}$, and R$^{iii}$ are each independently OH, alkoxy or H;

R$^{iv}$, R$^v$, R$^{viii}$ and R$^{ix}$, are each independently H, alkyl, cycloalkyl or -alkylene-N(alkyl)$_2$; and x is 0, 1 or 2.

It is to be understood that heterocycloalkyl is as defined above, and is unsubstituted or substituted as defined above. Phenyl and heteroaryl are as defined above, and are unsubstituted or substituted as defined above.

In certain embodiments,

R$^i$, R$^{ii}$, and R$^{iii}$ are each independently OH or H; and

R$^{iv}$, R$^v$, R$^{vi}$, R$^{vii}$, R$^{viii}$ and R$^{ix}$, are each independently H, alkyl, or cycloalkyl.

In certain embodiments, R$^2$ is as defined above.

In certain embodiments, R$^2$ is selected from indan-1-yl, indan-2-yl, benzofuran-3-yl, or 1,2,3,4-tetrahydronaphthalen-1-yl, each unsubstituted or independently substituted on the benzo moiety with one, two or three alkoxy, halo, alkyl and haloalkyl.

In certain embodiments, R$^2$ is selected from indan-1-yl, indan-2-yl, benzofuran-3-yl, or 1,2,3,4-tetrahydronaphthalen-1-yl, each unsubstituted or independently substituted on the benzo moiety with one, two or three alkoxy, and halo.

In certain embodiments, R$^2$ is selected from indan-1-yl, 7-methoxy-indan-1-yl, 5-fluoro-indan-1-yl, 4-methoxy-2,3-dihydro-benzofuran-3-yl, indan-2-yl, 6-methoxy-indan-1-yl, and 8-methoxy-1,2,3,4-tetrahydro-naphthalen-1-yl.

It is understood that all combinations of the specifically described embodiments above are encompassed by present invention.

Preferred compounds of formula I are those as shown in the examples below.

More preferred compounds of formula I are:

N$^2$-(R)-Indan-1-yl-N$^5$-methyl-quinoline-2,5-diamine,

N$^2$-(R)-Indan-1-yl-N$^5$-(tetrahydro-pyran-4-yl)-quinoline-2,5-diamine,

N$^2$-(R)-Indan-1-yl-N$^5$-(2-methylsulfanyl-ethyl)-quinoline-2,5-diamine,

N$^2$-(R)-Indan-1-yl-N$^5$-(2-methanesulfinyl-ethyl)-quinoline-2,5-diamine,

N$^2$-(R)-Indan-1-yl-N$^5$-(2-methanesulfonyl-ethyl)-quinoline-2,5-diamine, (R)—N$^2$-Indan-1-yl-quinoline-2,5-diamine, Cyclopropanesulfonic acid[2-((R)-indan-1-ylamino)-quinolin-5-yl]-amide, rac-N$^2$-(7-Methoxy-indan-1-yl)-quinoline-2,5-diamine, rac-N'-{2-[(7-methoxy-indan-1-yl)amino]quinolin-5-yl}-N,N-dimethylsulfamide, N-Hydroxy-2-((R)-indan-1-ylamino)-quinoline-5-carboxamidine, Cyclopropyl-[2-((R)-indan-1-ylamino)-quinolin-5-yl]-methanone oxime, rac-N$^2$-(5-Fluoro-indan-1-yl)-quinoline-2,5-diamine, rac-N$^2$-(4-Methoxy-2,3-dihydro-benzofuran-3-yl)-N$^5$-(2-methylsulfanyl-ethyl)-quinoline-2,5-diamine, N$^5$-(2-Methanesulfonyl-ethyl)-N$^2$-(RS)-(4-methoxy-2,3-dihydro-benzofuran-3-yl)-quinoline-2,5-diamine, (5-Cyclopropyl-quinolin-2-yl)-(R)-indan-1-yl-amine, 2-(4-Fluoro-phenyl)-N-[2-((R)-indan-1-ylamino)-quinolin-5-yl]-acetamide, rac-N-[2-(5-Fluoro-indan-1-ylamino)-quinolin-5-yl]-2-(4-fluoro-phenyl)-acetamide, rac-2-(4-Chloro-phenyl)-N-[2-(5-fluoro-indan-1-ylamino)-quinolin-5-yl]-acetamide, rac-2-(4-Fluoro-phenyl)-N-[2-(7-methoxy-indan-1-ylamino)-quinolin-5-yl]-acetamide, rac-2-(4-Chloro-phenyl)-N-[2-(7-methoxy-indan-1-ylamino)-quinolin-5-yl]-acetamide, 2-(3,5-Difluoro-phenyl)-N-[2-((R)-indan-1-ylamino)-quinolin-5-yl]-acetamide, and 2-(4-Chloro-phenyl)-N-[2-((R)-indan-1-ylamino)-quinolin-5-yl]-acetamide.

The present compounds of formula I, their starting materials, their pharmaceutically acceptable salts, and their optical isomers can be prepared by methods known in the art.

For example, a process to synthesize representative compounds of formula I

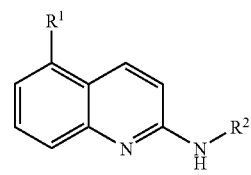

I can be used which comprises one of the following steps:
a) reacting a compound 2

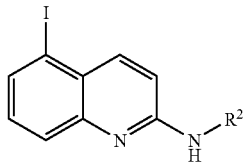

2 with an amine of formula $R^A R^B NH$ in a palladium catalyzed substitution reaction, wherein $R^A$ and $R^B$ are selected from H, alkyl, cycloalkyl, -alkylene-S-alkyl, -alkylene-$NR^{viii}R^{ix}$, heterocycloalkyl, -alkylene-cycloalkyl, -alkylene-O-alkyl, or $R^A$ and $R^B$ together form a cyclic amine, to give a compound of formula I wherein $R^1$ is —$NR^a R^b$ and wherein $R^a$ and $R^b$ are each independently H, alkyl, cycloalkyl, -alkylene-$S(O)_x$-alkyl, -alkylene-$N^{viii}R^{ix}$, heterocycloalkyl, -alkylene-cycloalkyl, or -alkylene-O-alkyl, with x being 0, and $R^{viii}$ and $R^{ix}$ are each independently H, alkyl, cycloalkyl or -alkylene-$N(alkyl)_2$; or $R^1$ is heterocycloalkyl (attached via a nitrogen atom). Preferably, $R^{viii}$ and $R^{ix}$ are each independently H, alkyl or cycloalkyl.
b) reacting a compound of formula 8

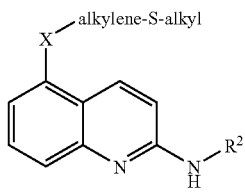

8 wherein X is NH or O with meta-chloro-perbenzoic acid to obtain a compound of formula I wherein $R^1$ is —$NR^a R^b$ and wherein $R^a$ is H and $R^b$ is -alkylene-$S(O)_x$-alkyl, with x being 1 or 2;
c) reducing compound 4

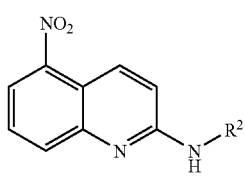

4 in the presence of a palladium catalyst to give a compound of formula I wherein $R^1$ is $NH_2$;
d) reacting a compound of formula I with $R^1$ being $NH_2$ with either a compound of formula $R^D SO_2 Cl$ or a compound of formula $R^{iv} R'NSO_2 Cl$ to give a compound of formula I wherein $R^1$ is —$NR^a R^b$ with $R^a$ being H and $R^b$ being —$S(O)_2$-alkyl, —$S(O)_2$-cycloalkyl or —$S(O)_2 NR^{iv}R^v$; wherein $R^{iv}$ and $R^v$ are each independently H, alkyl, cycloalkyl or -alkylene-$N(alkyl)_2$;
e) reacting a compound of formula I with $R^1$ being $NH_2$ with a compound of formula $R^E C(O)LG$, wherein LG is Cl or $R^E C(O)LG$ is an activated ester formed in situ with a coupling agent, and $R^E$ is cycloalkyl, alkyl, alkylene-heterocycloalkyl, heterocycloalkyl, alkylene-$NR^{viii}R^{ix}$, alkylene-O-alkyl, —$CH_2$-phenyl, or —$CH_2$-heteroaryl, and wherein phenyl or heteroaryl are each individually unsubstituted or substituted as described herein,
to give a compound of formula I, wherein $R^1$ is —$NR^a R^b$ with $R^a$ being H and $R^b$ being C(O)-cycloalkyl, —C(O)alkyl, —C(O)-alkylene-heterocycloalkyl, —C(O)-heterocycloalkyl, —C(O)-alkylene-$NR^{viii}R^{ix}$, —C(O)-alkylene-O-alkyl, —C(O)—$CH_2$-phenyl, or —C(O)—$CH_2$-heteroaryl; $R^{viii}$ and $R^{ix}$, are each independently H, alkyl, cycloalkyl or -alkylene-$N(alkyl)_2$;
f) reacting a compound of formula 5

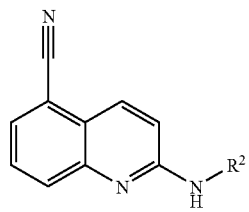

5 f1) with hydroxylamine, to give a compound of formula I wherein $R^1$ is —C(=N—OH)$NH_2$;
f2) with Raney nickel and hydrogen, to give a compound of formula I wherein $R^1$ is —$CH_2 NH_2$;
f3) with a Grignard reagent of formula $R^F MgHal$ wherein $R^F$ is alkyl or cycloalkyl, to give a compound of formula I wherein $R^1$ is —C(O)alkyl or —C(O)cycloalkyl;
g) reacting the product of step f3 with either $NH_2OH$ or $NH_2Oalkyl$, to give a compound of formula I with $R^1$ being —C(=N—OH)alkyl, —C(=N—OH)cycloalkyl, —C(=N—Oalkyl)alkyl, or —C(=N—Oalkyl)cycloalkyl;
h) reacting a compound of formula 2

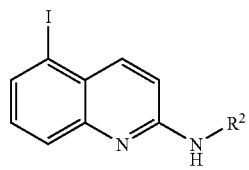

2 with a boronic acid of formula $R^1 B(OH)_2$ and a palladium catalyst, wherein $R^1$ is alkyl or cycloalkyl, to give a product of formula I wherein $R^1$ is alkyl or cycloalkyl;
i) reacting a compound of formula 7

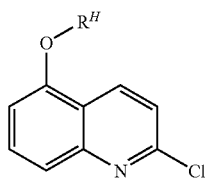

7 wherein $R^H$ is alkyl, alkylene-O-alkyl, or alkylene-S-alkyl with an amine of formula $NH_2 R^2$, and wherein $R^2$ is as defined above,
to give a compound of formula I wherein $R^1$ is —Oalkyl, —O-alkylene-O-alkyl, or —O-alkylene-S-alkyl;
j) reacting a compound of formula I wherein $R^1$ is —$NH_2$ with triphosgene and an amine of formula $HNR^I R^J$ wherein $R^I$ and $R^J$ are each independently H, alkyl, cycloalkyl, or alkylene-$N(alkyl)_2$, or $R^I$ and $R^J$ together with the nitrogen to which they are bound form a heterocycloalkyl, to give a compound of formula I wherein $R^1$ is —$NR^aR^b$ with $R^a$ being H and $R^b$ being —$C(O)NR^{iv}R^v$, wherein $R^{iv}$ and $R^v$ are alkyl, cycloalkyl, or alkylene-$N(alkyl)_2$, or wherein $R^1$ is —C(O)-heterocycloalkyl.

It can be stated that present invention also encompasses the products produced by the above-given processes.

As mentioned earlier, the compounds of formula I and their pharmaceutically acceptable addition salts possess valuable pharmaceutical properties. It has been found that the compounds of the present invention are active on the 5-$HT_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

Test Description

A [$^3$H]LSD radioligand binding assay was used to determine the affinity of the compounds for the recombinant human 5-$HT_{5A}$ receptor, in membranes from transiently (cDNA) expressed 5-$HT_{5A}$ receptors in Human Embryonic Kidney-EBNA (HEK-EBNA) cells. Assay buffer consisted of Tris (50 mM) buffer containing 1 mM EGTA, 10 mM $MgCl_2$ (pH 7.4) and 10 μM pargyline. The binding assay was carried out in 96-well-plates in the presence of [$^3$H]LSD (approximately 1 nM), approximately 2 μg/well of membrane protein, and 0.5 mg of Ysi-poly-1-lysine SPA beads in a final volume of 200 μl of buffer. Non-specific binding was defined using methiothepin 2 μM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. $IC_{50}$ values were calculated using a non-linear curve fitting program and Ki values calculated using the Cheng-Prussoff equation.

The activity of the compounds according to the invention is exemplified in the table 1 below:

| Example | Ki/nM | Example | Ki/nM | Example | Ki/nM |
|---|---|---|---|---|---|
| 1 | 22.5 | 28 | 17.4 | 54 | 11.0 |
| 3 | 26.0 | 31 | 5.8 | 57 | 9.1 |
| 5 | 23.5 | 37 | 12.5 | 59 | 28.7 |
| 6 | 26.5 | 39 | 25.2 | 60 | 5.5 |
| 7 | 24.7 | 40 | 29.1 | 4 | 104.8 |
| 16 | 7.2 | 44 | 27.7 | 22 | 68.0 |
| 17 | 32.2 | 45 | 11.0 | 23 | 218.7 |
| 19 | 6.1 | 48 | 17.6 | 24 | 90.6 |
| 20 | 2.3 | 51 | 9.4 | 46 | 36.1 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. gelatinLactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | mg/capsule | | | |
|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Preparation of the coounds of present invention:

Compounds of formula I can be prepared in accordance with the following routes:

Route 1 is Described in Example 1

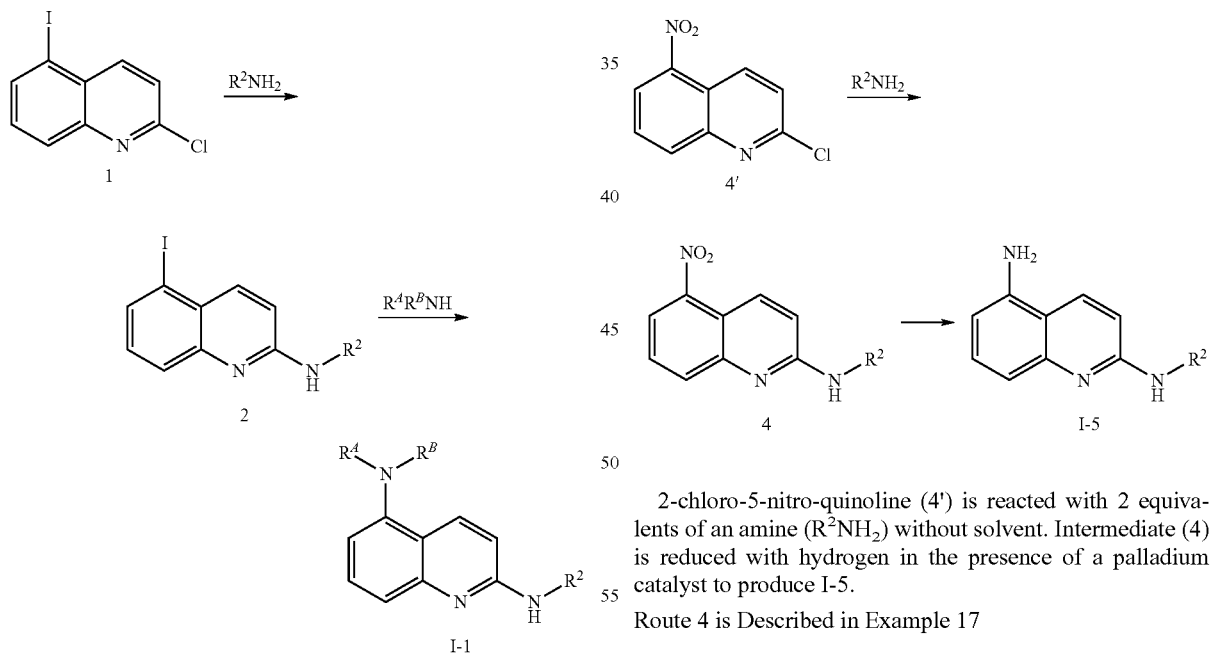

5-Iodo-2-chloroquinoline (2) is reacted with 2 equivalents of an amine ($R^2NH_2$) without solvent. Intermediate (2) is reacted with another amine ($R^AR^BNH$) in a palladium catalyzed substitution reaction. Thereby, $R^A$ and $R^B$ are selected from H, alkyl, -alkylene-S-alkyl, -alkylene-$NR^{viii}R^{ix}$, heterocycloalkyl, or $R^A$ and $R^B$ together form a cyclic amine. $R^{viii}$ and $R^{ix}$ are each independently H, alkyl, —C(O)Oalkyl, cycloalkyl, or heterocycloalkyl.

Route 2 is Described in Example 6 and 7

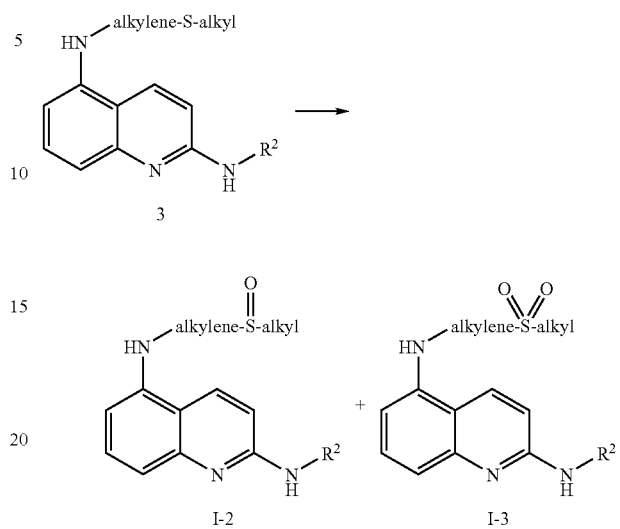

Sulfide (3) is reacted with 2 equivalents of meta-chloroperbenzoic acid to obtain of mixture of the corresponding sulfoxide (I-2) and sulfon (I-3) which could be separated by column chromatography.

Route 3 is Described in Example 16

2-chloro-5-nitro-quinoline (4') is reacted with 2 equivalents of an amine ($R^2NH_2$) without solvent. Intermediate (4) is reduced with hydrogen in the presence of a palladium catalyst to produce I-5.

Route 4 is Described in Example 17

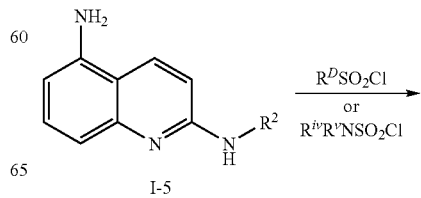

-continued

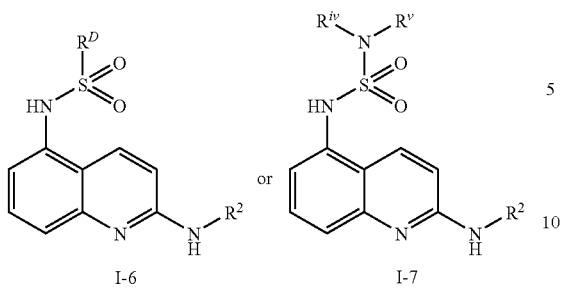

I-6 or I-7

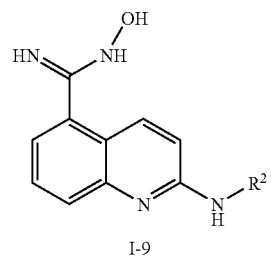

I-9

Amine (I-5) is reacted with a sulfonyl or sulfamoyl chloride to produce sulfonamide I-6 or sulfamide I-7. Thereby, $R^D$ is alkyl or cycloalkyl, and $R^{iv}$, $R^v$ and $R^2$ are as described above.

Route 5 is Described in Example 18

Reaction of cyano derivatives 5 (see route 8) with hydroxylamine to the corresponding amidoximes I-9.

Route 7 is Described in Example 29

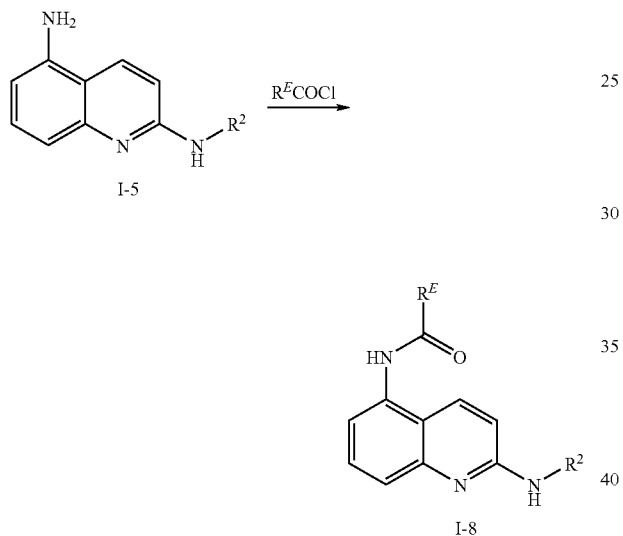

I-5

I-8

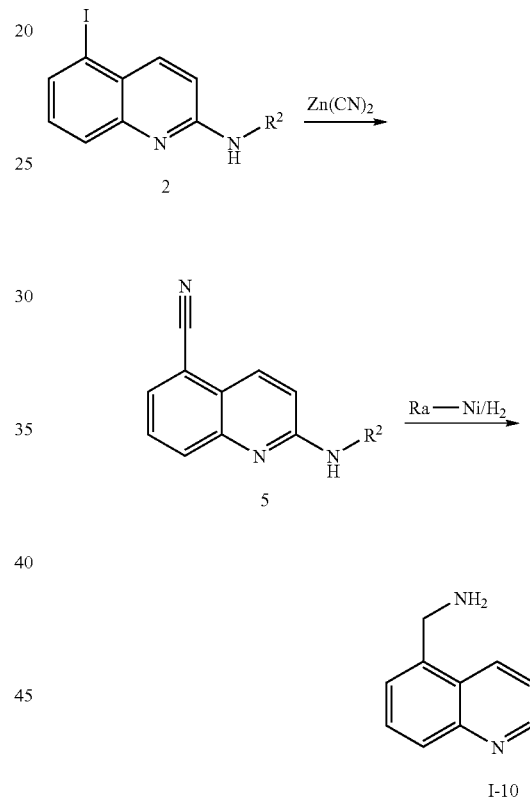

2

5

I-10

Amine (I-5) is reacted with an acid chloride to produce carboxamide I-8. In principle, this synthesis route is available wherein $R^E$ is cycloalkyl, alkyl, alkylene-heterocycloalkyl, heterocycloalkyl, alkylene-$NR^{viii}R^{ix}$, alkylene-O-alkyl, —$CH_2$-phenyl, or —$CH_2$-heteroaryl wherein phenyl or heteroaryl are each individually unsubstituted or substituted as described herein. Alternatively, synthesis route 10 can be chosen.

Route 6 is Described in Example 28

Intermediates 2 (see route 1) are reacted with zinc cyanide in a palladium catalyzed substitution reaction. The cyano group in 5 is reduced by hydrogenation to the amines I-10.

Route 8 is Described in Example 30

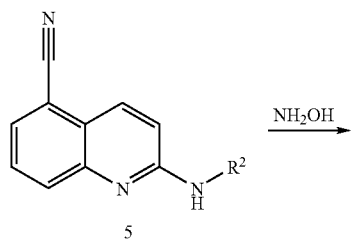

5

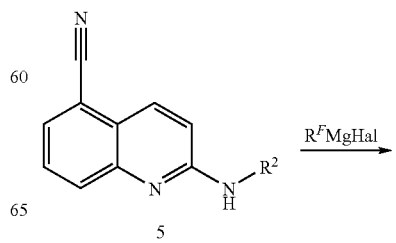

5

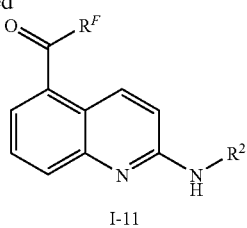

I-11

Reaction of cyano derivatives 5 with alkyl Grignard reagents ($R^F$MgHal). Thereby, $R^F$ is alkyl or cycloalkyl, and $R^2$ is as defined herein.

Route 9 is Described in Example 31

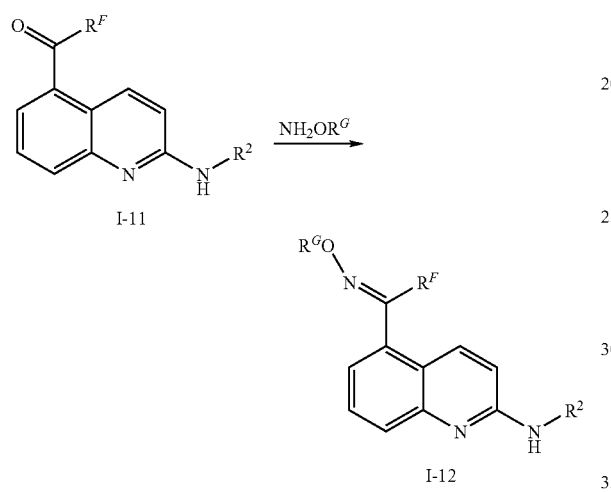

Reaction of ketones I-11 with hydroxylamines to the corresponding oximes I-12. Thereby, $R^G$ is H or alkyl, $R^F$ is alkyl or cycloalkyl, and $R^2$ is as defined herein.

Route 10 is Described in Example 32

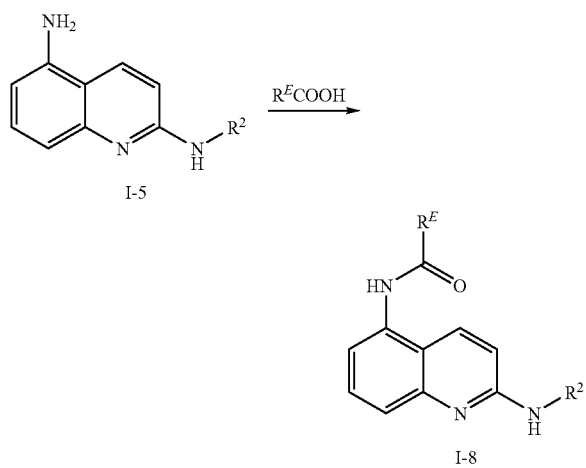

Reaction of 5-amino-quinolines I-5 with carboxylic acid derivatives to the amides I-8. In principle, this synthesis route is available wherein $R^E$ is cycloalkyl, alkyl, alkylene-heterocycloalkyl, heterocycloalkyl, alkylene-$NR^{viii}R^{ix}$, alkylene-O-alkyl, —CH$_2$-phenyl, or —CH$_2$-heteroaryl wherein phenyl or heteroaryl are each individually unsubstituted or substituted as described herein. The following coupling reagents can be chosen: a mixture of N-ethyldiisopropylamine and O-(benzotriazol-1-yl)-N,N,N',N'-tetramethyluronium-tetrafluoroborate (TBTU).

Alternatives might be O-(benzotriazol-1-yl)-N,N,N',N'-tetramethyluronium-hexafluoroborate (HBTU), benzotriazol-1-yloxy)-tris-(dimethylamino)-phosphonium-hexafluorophosphate (BOP), benzotriazol-1-yloxy)-tripyrrolidinophosphonium-hexafluorophosphate (PyBOP), O-(benzotriazol-1-yl)-N,N,N',N'-bis-(tetramethylen)-uronium-hexafluorophosphate (HBPyU). Alternatively, synthesis route 5 can be chosen.

Route 11 is Described in Example 44

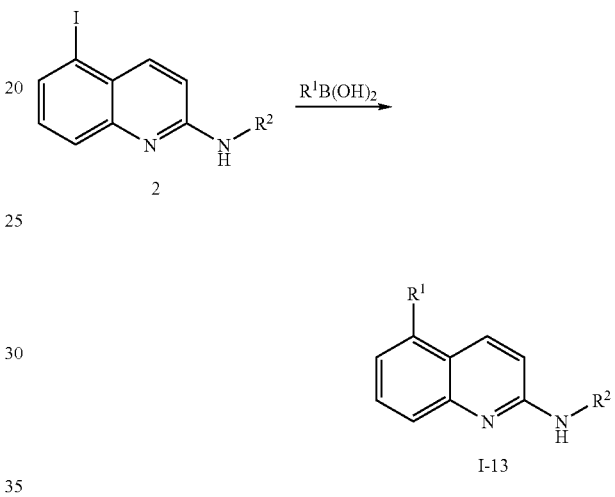

Intermediates 2 (see route 1) are reacted with a boronic acid $R^1B(OH)_2$ in a palladium catalyzed substitution reaction to the product I-13. Thereby, $R^1$ is selected from alkyl or cycloalkyl.

Route 12 is Described in Example 24

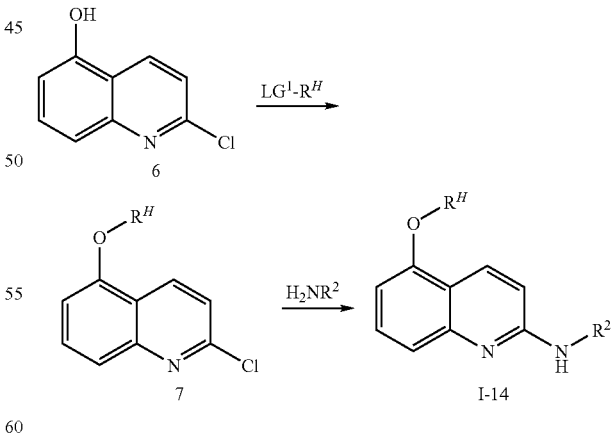

Compound 6 (CAS-RN: 124467-35-2) is reacted with $LG^1$-$R^H$, for instance with bromo-ethyl-methylether to yield intermediate I-14 which then is treated with an amine to yield final product I-14. Thereby $R^H$ is selected from alkyl, alkylene-O-alkyl, or alkylene-S-alkyl, $R^2$ is as defined above and $LG^1$ is halo or OH, preferably Br or Cl.

Route 13 is Described in Example 26 and 27

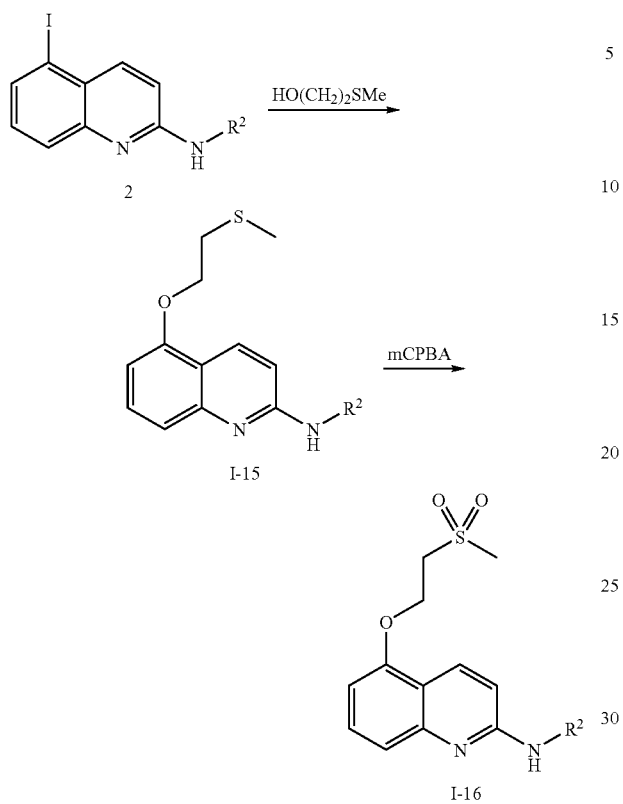

Intermediate 2 is reacted with 2-methylsulfanyl-ethanol in a copper catalyzed substitution reaction to the sulfide I-15 which was oxidized with meta-chloro-perbenzoic acid to the sulfone I-16.

Route 14 as Described in Example 36

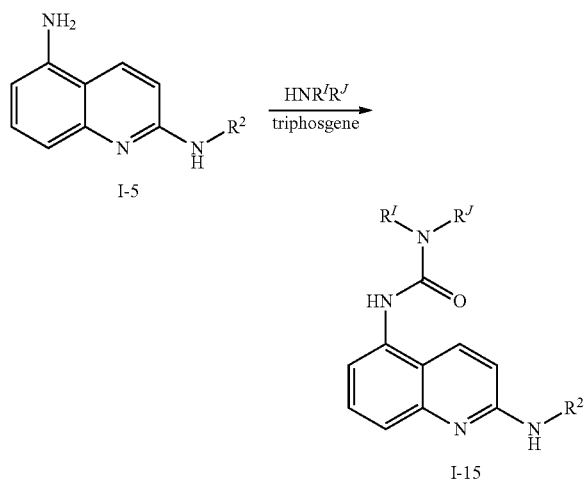

Intermediate I-5 is reacted with triphosgene, followed by reaction with an amine of formula $HNR^IR^J$ to give a compound of formula I-15. Thereby, $R^I$ and $R^J$ are selected from H, alkyl, cycloalkyl, or alkylene-N(alkyl)$_2$, or $R^I$ and $R^J$ together with the nitrogen to which they are bound form a heterocycloalkyl, for instance 4-methylpiperazin-1-yl.

EXAMPLES

Example 1

$N^2$-(R)-Indan-1-yl-$N^5$-methyl-quinoline-2,5-diamine

Step A: 5-Iodo-2-chloroquinoline (CAS 455955-26-7, 5.0 g, 17 mmol) and (R)-1-aminoindane (4.75 g, 35 mmol) were stirred in a sealed tube at 120° C. for 2 days. The reaction mixture was purified by flash chromatography on silica gel (cyclohexane/ethyl acetate 100:0→80:20 gradient). (R)-Indan-1-yl-(5-iodo-quinolin-2-yl)-amine was obtained as a brown solid (4.30 g, 64%), MS: m/e=387.3 (M+H$^1$).

Step B: (R)-Indan-1-yl-(5-iodo-quinolin-2-yl)-amine (500 mg, 1.3 mmol) was dissolved in 4 mL dioxane. Argon was bubbled through the solution for 2 minutes to remove oxygen. Methylamine (33% in ethanol, 0.48 mL, 4 mmol), sodium tert.-butylate (321 mg, 3.3 mmol), 1,1'-bis(diphenylphosphin)ferrocen (111 mg, 0.2 mmol) and 1,1'-bis(diphenylphosphin)ferrocen-palladium(II)chloride (53 mg, 0.06 mmol) were added. The reaction mixture was stirred in a sealed tube at 120° C. overnight. The solvent was evaporated and the residue purified by flash chromatography on silica gel (heptane/ethyl acetate 100:0→50:50 gradient). The title compound was obtained as a brown oil (110 mg, 29%), MS: m/e=290.1 (M+H$^+$).

Example 2

$N^5$-Cyclopropylmethyl-$N^2$-(R)-indan-1-yl-quinoline-2,5-diamine

The title compound, MS: m/e=330.4 (M+H$^+$), was prepared in accordance with the general method of example 1 from 5-iodo-2-chloroquinoline, (R)-1-aminoindane and aminomethyl cyclopropane.

Example 3

$N^2$-(R)-Indan-1-yl-$N^5$-(tetrahydro-pyran-4-yl)-quinoline-2,5-diamine

The title compound, MS: m/e=360.3 (M+H$^+$), was prepared in accordance with the general method of example 1 from 5-iodo-2-chloroquinoline, (R)-1-aminoindane and 4-amino-tetrahydropyran.

Example 4

(R)-Indan-1-yl-(5-morpholin-4-yl-quinolin-2-yl)-amine

The title compound, MS: m/e=346.4 (M+H$^+$), was prepared in accordance with the general method of example 1 from 5-iodo-2-chloroquinoline, (R)-1-aminoindane and morpholine.

Example 5

$N^2$-(R)-Indan-1-yl-$N^5$-(2-methylsulfanyl-ethyl)-quinoline-2,5-diamine

The title compound, MS: m/e=350.5 (M+H$^+$), was prepared in accordance with the general method of example 1 from 5-iodo-2-chloroquinoline, (R)-1-aminoindane and 2-(methylthio)ethylamine.

Example 6

N²-(R)-Indan-1-yl-N⁵-(2-methanesulfinyl-ethyl)-quinoline-2,5-diamine

N²-(R)-Indan-1-yl-N⁵-(2-methylsulfanyl-ethyl)-quinoline-2,5-diamine (200 mg, 0.57 mmol) were dissolved in 5.5 mL dichloromethane and meta-chloro-perbenzoic acid was added (207 mg, 1.2 mmol). The reaction mixture was stirred at room temperature overnight. The reaction mixture was quenched by addition of 10 mL water and 10 mL 2N sodium carbonate solution. The mixture was extracted three times with ethyl acetate (50 mL each). The organic phases ware pooled, dried with sodium sulfate, filtered and evaporated. The reaction mixture was purified by flash chromatography on silica gel (dichloromethane/methanol 100:0→90:10 gradient). The title compound was obtained as a light brown solid (113 mg, 54%), MS: m/e=366.3 (M+H⁺) together with N²-(R)-indan-1-yl-N⁵-(2-methanesulfonyl-ethyl)-quinoline-2,5-diamine.

Example 7

N²-(R)-Indan-1-yl-N⁵-(2-methanesulfonyl-ethyl)-quinoline-2,5-diamine

N²-(R)-Indan-1-yl-N⁵-(2-methylsulfanyl-ethyl)-quinoline-2,5-diamine (200 mg, 0.57 mmol) were dissolved in 5.5 mL dichloromethane and meta-chloro-perbenzoic acid was added (207 mg, 1.2 mmol). The reaction mixture was stirred at room temperature overnight. The reaction mixture was quenched by addition of 10 mL water and 10 mL 2N sodium carbonate solution. The mixture was extracted three times with ethyl acetate (50 mL each). The organic phases ware pooled, dried with sodium sulfate, filtered and evaporated. The reaction mixture was purified by flash chromatography on silica gel (dichloromethane/methanol 100:0→90:10 gradient). The title compound was obtained as a light brown solid (65 mg, 30%), MS: m/e=382.5 (M+H⁺) together with N2-(R)-indan-1-yl-N5-(2-methanesulfinyl-ethyl)-quinoline-2,5-diamine.

Example 8

N⁵-(2-Dimethylamino-ethyl)-N²-(R)-indan-1-yl-quinoline-2,5-diamine

The title compound, MS: m/e=347.4 (M+H⁺), was prepared in accordance with the general method of example 1 from 5-iodo-2-chloroquinoline, (R)-1-aminoindane and N,N-dimethylethylenediamine.

Example 9 rac-N⁵-(1,1-Dioxo-tetrahydro-thiophen-3-yl)-N²-(6-methoxy-indan-1-yl)-quinoline-2,5-diamine The title compound, MS: m/e=424.3 (M+H⁺), was prepared in accordance with the general method of example 1 from 5-iodo-2-chloroquinoline, 6-methoxyindan-1-ylamine (CAS 103028-81-5) and 1,1-dioxido-tetrahydrothien-3-ylamine.

Example 10 rac-N²-(6-Methoxy-indan-1-yl)-N⁵-(2-methylsulfanyl-ethyl)-quinoline-2,5-diamine

The title compound, MS: m/e=380.5 (M+H⁺), was prepared in accordance with the general method of example 1 from 5-iodo-2-chloroquinoline, 6-methoxyindan-1-ylamine (CAS 103028-81-5) and 2-(methylthio)ethylamine.

Example 11 rac-N⁵-(2-Methanesulfinyl-ethyl)-N²-(6-methoxy-indan-1-yl)-quinoline-2,5-diamine The title compound, MS: m/e=396.4 (M+H⁺), was prepared in accordance with the general method of example 6 from N2-(6-methoxy-indan-1-yl)-N5-(2-methylsulfanyl-ethyl)-quinoline-2,5-diamine.

Example 12 rac-N⁵-(2-Methanesulfonyl-ethyl)-N²-(6-methoxy-indan-1-yl)-quinoline-2,5-diamine The title compound, MS: m/e=412.4 (M+H⁺), was prepared in accordance with the general method of example 7 from N²-(6-methoxy-indan-1-yl)-N⁵-(2-methylsulfanyl-ethyl)-quinoline-2,5-diamine.

Example 13 rac-N²-(6-Methoxy-indan-1-yl)-N⁵-(3-methylsulfanyl-propyl)-quinoline-2,5-diamine The title compound, MS: m/e=394.3 (M+H⁺), was prepared in accordance with the general method of example 1 from 5-iodo-2-chloroquinoline, 6-methoxyindan-1-ylamine (CAS 103028-81-5) and 3-(methylthio)propylamine.

Example 14 rac-N⁵-(3-Methanesulfonyl-propyl)-N²-(6-methoxy-indan-1-yl)-quinoline-2,5-diamine The title compound, MS: m/e=426.1 (M+H⁺), was prepared in accordance with the general method of example 7 from N²-(6-methoxy-indan-1-yl)-N⁵-(3-methylsulfanyl-propyl)-quinoline-2,5-diamine.

Example 15 rac-N⁵-(3-Methanesulfinyl-propyl)-N²-(6-methoxy-indan-1-yl)-quinoline-2,5-diamine The title compound, MS: m/e=410.3 (M+H⁺), was prepared in accordance with the general method of example 6 from N²-(6-methoxy-indan-1-yl)-N⁵-(3-methylsulfanyl-propyl)-quinoline-2,5-diamine.

Example 16

(R)—N²-Indan-1-yl-quinoline-2,5-diamine

Step A: 5-Nitro-2-chloroquinoline (CAS 13067-94-2, 2.4 g, 11.5 mmol) and (R)-1-aminoindane (3.13 g, 23 mmol) were stirred in a sealed tube at 120° C. overnight. The reaction mixture was purified by flash chromatography on silica gel (cyclohexane/ethyl acetate 100:0→50:50 gradient). (R)-Indan-1-yl-(5-nitro-quinolin-2-yl)-amine was obtained as a brown solid (2.67 g, 76%), MS: m/e=306.3 (M+H⁺).

Step B: (R)-Indan-1-yl-(5-nitro-quinolin-2-yl)-amine (2.66 g, 8.7 mmol) was dissolved in 420 mL ethanol. Palladium on charcoal (10%, 463 mg, 0.4 mmol) was added and

Example 17

Cyclopropanesulfonic acid[2-((R)-indan-1-ylamino)-quinolin-5-yl]-amide (R)—$N^2$-Indan-1-yl-quinoline-2,5-diamine (200 mg, 0.73 mmol) was dissolved in 2 mL pyridine and cyclopropane sulfonylchloride (102 mg, 0.73 mmol) was added. The reaction mixture was stirred at room temperature overnight and quenched by addition of 50 mL water and acetic acid until pH 5. The mixture was extracted three times with ethyl acetate (50 mL each). The organic phases ware pooled, dried with sodium sulfate, filtered and evaporated. The residue was purified by flash chromatography on silica gel (cyclohexane/ethyl acetate 100:0→50:50 gradient). The title compound was obtained as a brown solid (160 mg, 58%), MS: m/e=380.4 (M+H$^+$).

Example 18

N-[2-((R)-Indan-1-ylamino)-quinolin-5-yl]-3-methoxy-propionamide (R)—$N^2$-Indan-1-yl-quinoline-2,5-diamine (150 mg, 0.55 mmol) was dissolved in 3 mL pyridine and 3-methoxypropionyl chloride (70 mg, 0.0.57 mmol) and 4-dimethylamino pyridine (3 mg, 0.02 mmol) were added. The reaction mixture was stirred at 80° C. overnight and quenched by addition of 50 mL water and acetic acid until pH 5. The mixture was extracted three times with ethyl acetate (50 mL each). The organic phases ware pooled, dried with sodium sulfate, filtered and evaporated. The residue was purified by flash chromatography on silica gel (cyclohexane/ethyl acetate 100:0→0:100 gradient). The title compound was obtained as a brown solid (59 mg, 30%), MS: m/e=362.4 (M+H$^-$).

Example 19 rac-$N^2$-(7-Methoxy-indan-1-yl)-quinoline-2,5-diamine

The title compound, MS: m/e=306.4 (M+H$^+$), was prepared in accordance with the general method of example 16 from 5-nitro-2-chloroquinoline and 7-methoxy-indane-1-ylamine.

Example 20 rac-N'-{2-[(7-methoxy-indan-1-yl)amino]quinolin-5-yl}-N,N-dimethylsulfamide

The title compound, MS: m/e=413.4 (M+H$^+$), was prepared in accordance with the general method of example 17 from $N^2$-(7-methoxy-indan-1-yl)-quinoline-2,5-diamine and dimethyl sulfamoyl chloride.

Example 21 rac-$N^2$-(8-Methoxy-1,2,3,4-tetrahydro-naphthalen-1-yl)-quinoline-2,5-diamine

The title compound, MS: m/e=320.4 (M+H$^+$), was prepared in accordance with the general method of example 16 from 5-nitro-2-chloroquinoline and 8-methoxy-1,2,3,4-tetrahydro-naphthalen-1-amine (CAS 535935-61-6).

Example 22

Cyclopropanecarboxylic acid[2-((R)-indan-1-ylamino)-quinolin-5-yl]-amide

The title compound, MS: m/e=344.3 (M+H$^+$), was prepared in accordance with the general method of example 18 from (R)—$N^2$-indan-1-yl-quinoline-2,5-diamine and cyclopropane carbonyl chloride.

Example 23 rac-$N^2$-Indan-2-yl-quinoline-2,5-diamine

The title compound, MS: m/e=276.0 (M+H$^+$), was prepared in accordance with the general method of example 16 from 5-nitro-2-chloroquinoline and indane-2-ylamine.

Example 24

(R)-Indan-1-yl-[5-(2-methoxy-ethoxy)-quinolin-2-yl]-amine

Step A: 2-Chloro-5-hydroxy-quinoline (0.30 g, 1.67 mmol) was dissolved in aceton (10 mL). Potassium carbonate (370 mg, 2.7 mmol) and bromo-ethyl-methylether (250 □L, 2.7 mmol) were added. The reaction mixture was stirred for 18 h at 50° C. After addition of water the reaction mixture was extracted with ethyl acetate (3×50 mL) and the combined organic phases were dried on sodium sulfate. After evaporation of the solvent a brown oil was obtained which was subjected to column chromatography (silica gel, heptane:ethyl acetate 9:1, 4:1) to yield 2-chloro-5-(2-methoxy-ethoxy)-quinoline as a colorless oil (120 mg, 30%); MS: m/e=238.8 (M+H$^+$).

Step B: The title compound (MS: m/e=335.6 (M+H$^+$)) was obtained according to the general method described in step A of example 1 from 2-chloro-5-(2-methoxy-ethoxy)-quinoline and (R)-1-aminoindane.

Example 25

(R)-Indan-1-yl-(5-methoxy-quinolin-2-yl)-amine

The title compound (MS: m/e=291.6 (M+H$^+$)) was obtained according to the general method described in step A of example 1 from 2-chloro-5-methoxy-quinoline (CAS-RN: 160893-07-2) and (R)-1-aminoindane.

Example 26

(R)-Indan-1-yl-[5-(2-methylsulfanyl-ethoxy)-quinolin-2-yl]-amine (R)-Indan-1-yl-(5-iodo-quinolin-2-yl)-amine (250 mg, 0.6 mmol) were dissolved in toluene (2 mL). 2-Hydroxyethyl-methylsulfide (0.17 □L, 1.8 mmol), copper iodide (12 mg), cesium carbonate (420 mg, 1.2 mmol) and phenantroline (23 mg) were added. The reaction mixture was stirred for 48 h at 110° C. The reaction mixture was extracted with water (2×10 mL). The organic phase was dried on sodium sulfate and evaporated. The residue was subjected to column chromatography (silica gel, heptane:ethyl acetate 10:0→3:2) to yield the title compound as brown oil (80 mg, 35%); MS: m/e=351.6 (M+H$^+$).

Example 27

(R)-Indan-1-yl-[5-(2-methanesulfonyl-ethoxy)-quinolin-2-yl]-amine (R)-Indan-1-yl-[5-(2-methylsulfanyl-ethoxy)-quinolin-2-yl]-amine (64 mg, 0.2 mmol) were dissolved in dichloromethane (3.0 mL). meta-chloroperbenzoic acid (100 mg, 0.5 mmol) was added and the reaction mixture stirred for 3 h at ambient temperature. Sodium carbonate (1 M, 10 mL) was added and the aqueous phase extracted with dichloromethane (3×10 mL). The combined organic phases were dried on sodium sulfate, filtered and evaporated. The residue was subjected to column chromatography (silica gel, dichloromethane) to yield the title compound as a brown solid (26 mg; 37%); MS: m/e=383.7 (M+H$^+$).

Example 28

N-Hydroxy-2-((R)-indan-1-ylamino)-quinoline-5-carboxamidine

A stirred suspension of 2-((R)-indan-1-ylamino)-quinoline-5-carbonitrile (example 29, step A) (571 mg, 2.0 mmol), hydroxylamine hydrochloride (514 mg, 7.4 mmol), sodium carbonate (424 mg, 4.0 mmol) in ethanol (7.5 ml) and water (7.5 ml) was heated under reflux conditions for 24 h, water (40 ml) was added, and the mixture was extracted with ethyl acetate (3×75 ml). The combined organic layers were washed with brine (30 ml), dried (MgSO$_4$) and evaporated to yield the crude product as solid which was further purified by crystallization (dichloromethane/methanol) to yield N-hydroxy-2-((R)-indan-1-ylamino)-quinoline-5-carboxamidine as white solid (500 mg, 79%). MS: m/e=319.2 (M+H$^+$); m.p. 200.5° C.

Example 29

(5-Aminomethyl-quinolin-2-yl)-(R)-indan-1-yl-amine

Step A: A mixture of (R)-indan-1-yl-(5-iodo-quinolin-2-yl)-amine (example 1, step A) (1.44 g, 3.73 mmol), zinc cyanide (482 mg, 4.1 mmol) and tetrakis-(triphenylphosphine)-palladium (431 mg, 0.37 mmol) in dimethylformamide (20 ml) was heated at 160° C. for 15 min in a microwave reactor. The reaction mixture was poured into water (50 ml) and extracted with ethyl acetate (2×100 ml). The combined organic layers were washed with brine (50 ml), dried (MgSO$_4$) and evaporated. The crude product was purified by flash chromatography (ethyl acetate/heptane) on silica gel and crystallization (diethyl ether/hexane) to yield 2-((R)-indan-1-ylamino)-quinoline-5-carbonitrile as light yellow solid (840 mg, 79%). M.p. 150° C.; MS: m/e=286.2 (M+H$^+$).
Step B: Hydrogenation of 2-((R)-indan-1-ylamino)-quinoline-5-carbonitrile (200 mg, 0.7 mmol) dissolved in methanol (10 ml) and 7N MeOH—NH$_3$ (5 ml) on Ra—Ni (200 mg) for 23 h at room temperature yielded after removal of the catalyst by filtration and evaporation a yellow oil which was further purified by column chromatography (dichloromethane/MeOH/NH$_4$OH 15:1:0.1) on silica gel to yield (5-aminomethyl-quinolin-2-yl)-(R)-indan-1-yl-amine as light yellow oil (190 mg, 94%). MS: m/e=290.1 (M+H$^+$).

Example 30

Cyclopropyl-[2-((R)-indan-1-ylamino)-quinolin-5-yl]-methanone

To a cooled (ice bath) and stirred suspension of 2-((R)-indan-1-ylamino)-quinoline-5-carbonitrile (example 29, step A) (285 mg, 1.0 mmol) in tetrahydrofurane (5 ml) was added drop wise a 0.5 M solution of cyclopropyl-magnesium bromide (12 ml, 6.0 mmol), the reaction mixture was heated under reflux conditions for 48 h and poured into ice-water (20 ml). 2N HCl (10 ml) was added, the mixture was stirred at room temperature for 10 min, 3 N NaOH (10 ml) was added and the mixture was extracted with ethyl acetate (3×80 ml). The combined organic layers were washed with brine (50 ml), dried (MgSO$_4$) and evaporated. The crude product was further purified by flash chromatography on silica gel (ethyl acetate/heptane to yield 170 mg of the intermediate imine, which was dissolved in 2N HCl (6 ml) and tetrahydrofurane (1.5 ml). The mixture was stirred at room temperature for 17 h, poured into saturated NaHCO$_3$ solution (20 ml) and extracted with ethyl acetate (2×40 ml). The combined organic layers were washed with brine (50 ml), dried (MgSO$_4$) and evaporated. The crude product was purified by flash chromatography (ethyl acetate/heptane) on silica gel to yield the title compound as light yellow oil (240 mg, 73%). MS: m/e=329.4 (M+H$^+$).

Example 31

Cyclopropyl-[2-((R)-indan-1-ylamino)-quinolin-5-yl]-methanone oxime

A stirred suspension of cyclopropyl-[2-((R)-indan-1-ylamino)-quinolin-5-yl]-methanone (example 30) (150 mg, 0.46 mmol), hydroxylamine hydrochloride (95 mg, 1.37 mmol) and sodium carbonate (145 mg, 1.37 mmol) in ethanol (5 ml) was heated under reflux conditions for 18 h, the reaction mixture was poured into water (5 ml) and the mixture was stirred for 2 h. The precipitate was collected by filtration and further purified by flash chromatography on silica gel (heptane/ethyl acetate) to yield the title compound as off-white solid (72 mg, 46%). M.p. 151° C.; MS: m/e=344.1 (M+H$^+$).

Example 32

2-Dimethylamino-N-[2-((R)-indan-1-ylamino)-quinolin-5-yl]-acetamide

To a stirred solution of N,N-dimethylglycine (124 mg, 1.2 mmol) in dichloromethane (20 ml) and DMF (10 ml) were added at room temperature N-ethyldiisopropylamine (452 mg, 3.5 mmol) and TBTU (514 mg, 1.6 mmol) and the mixture was allowed to stir for 90 min. (R)—N2-indan-1-yl-quinoline-2,5-diamine (example 16) (275 mg, 1.0 mmol) was added and the reaction mixture was allowed to stir for 17 h, poured into sat. NaHCO$_3$ solution (30 ml) and extracted with dichloromethane (2×30 ml). The combined organic layers were washed with water (30 ml), dried (MgSO4) and evaporated. The crude product was further purified by flash chromatography on silica gel (heptane/ethyl acetate) and crystallization (ethyl acetate/heptane) to yield the title compound as white solid (210 mg, 58%). M.p. 153° C.; MS: m/e=361.2 (M+H$^+$).

Example 33

N-[2-((R)-Indan-1-ylamino)-quinolin-5-yl]-2-morpholin-4-yl-acetamide

The title compound, off-white solid, m.p. 179° C.; MS: m/e=403.5 (M+H$^+$), was prepared in accordance with the general method of example 32 from (R)—N$^2$-indan-1-yl-quinoline-2,5-diamine (example 16) and commercially available morpholine-4-yl-acetic acid.

Example 34

1-Methyl-piperidine-4-carboxylic acid[2-((R)-indan-1-ylamino)-quinolin-5-yl]-amide The title compound, white solid, m.p. 197° C.; MS: m/e=401.4 (M+H$^+$), was prepared in accordance with the general method of example 32 from (R)—N$^2$-indan-1-yl-quinoline-2,5-diamine (example 16) and commercially available 1-methyl-piperidine-4-carboxylic acid.

Example 35

N-[2-((R)-Indan-1-ylamino)-quinolin-5-yl]-2-(tetrahydro-pyran-4-yl)-acetamide

The title compound, white solid, m.p. 211° C.; MS: m/e=402.4 (M+H$^+$), was prepared in accordance with the general method of example 32 from (R)—N$^2$-indan-1-yl-quinoline-2,5-diamine (example 16) and commercially available tetrahydropyran-4-yl-acetic acid.

Example 36

4-Methyl-piperazine-1-carboxylic acid[2-((R)-indan-1-ylamino)-quinolin-5-yl]-amide To a stirred solution of (R)—N$^2$-indan-1-yl-quinoline-2,5-diamine (example 16) (138 mg, 0.5 mmol) in THF (10 ml) was added at 0° C. triethylamine (56 mg, 0.55 mmol) and triphosgen (66.7 mg, 0.23 mmol). The white suspension was heated under reflux conditions for 3 h and triethylamine (56 mg, 0.55 mmol) and 1-methylpiperazine (55 mg, 0.55 mmol) were added at room temperature. The reaction mixture was allowed to stir at 50° C. for 16 h and was extracted with dichloromethane (2×30 ml). The combined organic layers were washed with water (2×20 ml), dried (MgSO4) and evaporated. The crude product was further purified by flash chromatography on silica gel (dichloromethane/MeOH) and crystallization (diethyl ether/heptane) to yield the title compound as off-white solid (30 mg, 15%). M.p. 142° C.; MS: m/e=402.5 (M+H$^+$)

Example 37 rac-N$^2$-[5-Fluoro-indan-1-yl]-quinoline-2,5-diamine

The title compound, light yellow foam, MS: m/e=294.1 (M+H$^+$), was prepared in accordance with the general method of example 16 from 5-nitro-2-chloroquinoline (example 16, CAS 13067-94-2) and commercially available (RS)-5-fluoro-indane-1-ylamine.

Example 38

2-Dimethylamino-N-[2-(5-(RS)-fluoro-indan-1-ylamino)-quinolin-5-yl]-acetamide

The title compound, off-white solid, m.p. 164° C.; MS: m/e=379.3 (M+H$^+$), was prepared in accordance with the general method of example 32 from rac-N$^2$-(5-fluoro-indan-1-yl)-quinoline-2,5-diamine (example 37) and commercially available N,N-dimethylglycine.

Example 39 rac-N$^2$-(4-Methoxy-2,3-dihydro-benzofuran-3-yl)-N$^5$-(2-methylsulfanyl-ethyl)-quinoline-2,5-diamine Step A: A mixture of 4-methoxy-benzofuran-3-one (CAS 7169-35-9) (4.9 g, 19 mmol), sodium acetate (3.06 g, 38 mmol) and hydroxylamine hydrochloride (2.58 g, 38 mmol) in EtOH (40 ml) was refluxed for 6 h. Cooled to room temperature, filtered the precipitate off, washed with EtOH and dried in high vacuum to give 4-methoxy-benzofuran-3-one oxime as a white solid (5.93 g, 100%); MS: m/e=180.2 (M+H$^+$).

Step B: A mixture of the above described 4-methoxy-benzofuran-3-one oxime (6.15 g, 34.3 mmol) in EtOH (500 ml) with 10% Pd/C (6.15 g) was hydrogenated at 23° C. and atmospheric pressure for 18 h. Filtered the catalyst off, washed with EtOH, evaporated the filtrate totally and dried in high vacuum to give (RS)-4-methoxy-2,3-dihydro-benzofuran-3-ylamine as a light yellow oil (3.65 g, 64%); MS: m/e=166.2 (M+H$^1$).

Step C: The title compound, yellow oil, MS: m/e=382.2 (M+H$^+$), was prepared in accordance with the general method of example 1 from 5-iodo-2-chloroquinoline, (RS)-(4-methoxy-2,3-dihydro-benzofuran-3-ylamine and commercially available 2-(methylthio)ethylamine.

Example 40

N$^5$-(2-Methanesulfonyl-ethyl)-N$^2$-(RS)-(4-methoxy-2,3-dihydro-benzofuran-3-yl)-quinoline-2,5-diamine The title compound, light brown solid, m.p 188° C.; MS: m/e=414.4 (M+H$^+$), was prepared in accordance with the general method of example 7 from rac-N$^2$-(4-methoxy-2,3-dihydro-benzofuran-3-yl)-N$^5$-(2-methylsulfanyl-ethyl)-quinoline-2,5-diamine (example 39).

Example 41 rac-N$^2$-(4-Methoxy-2,3-dihydro-benzofuran-3-yl)-N$^5$-(tetrahydro-pyran-4-yl)-quinoline-2,5-diamine The title compound, light yellow foam, MS: m/e=392.3 (M+H$^+$), was prepared in accordance with the general method of example 1 from 5-iodo-2-chloroquinoline, (RS)-4-methoxy-2,3-dihydro-benzofuran-3-ylamine (example 39, step A and B) and commercially available 4-amino-tetrahydropyran.

Example 42

N-[2-(RS)-(7-Methoxy-indan-1-ylamino)-quinolin-5-yl]-2-(4-methyl-piperazin-1-yl)-acetamide The title compound, light yellow oil, MS: m/e=446.2 (M+H$^+$), was prepared in accordance with the general method of example 32 from rac-N²-(7-methoxy-indan-1-yl)-quinoline-2,5-diamine (example 19) and commercially available (4-methyl-piperazin-1-yl)-acetic acid.

Example 43

N-[2-((S)-Indan-1-ylamino)-quinolin-5-yl]-2-(4-methyl-piperazin-1-yl)-acetamide

The title compound, light yellow oil, MS: m/e=416.4 (M+H⁺), was prepared in accordance with the general method of example 32 from (R)—N²-indan-1-yl-quinoline-2,5-diamine (example 16) and commercially available (4-methyl-piperazin-1-yl)-acetic acid.

Example 44

(5-Cyclopropyl-quinolin-2-yl)-(R)-indan-1-yl-amine (R)-Indan-1-yl-(5-iodo-quinolin-2-yl)-amine (example 1, step A, 2000 mg, 0.52 mmol) was dissolved in 5 mL toluene and 0.15 mL water. Cyclopropylboronic acid (89 mg, 1.04 mmol) was added. Argon was bubbled through the solution for 2 minutes to remove oxygen. Tri(cyclohexyl)-phosphine (30 mg, 0.11 mmol), palladium acetate (12 mg, 0.05 mmol) and tri-potassium phosphate (385 mg, 1.8 mmol) were added. The reaction mixture was evaporated. The residue was purified by flash chromatography on silica gel (heptane/ethyl acetate 100:0→75:25 gradient). The title compound was obtained as a white gum (114 mg, 73%), MS: m/e=301.3 (M+H⁺).

Example 45

2-(4-Fluoro-phenyl)-N-[2-((R)-indan-1-ylamino)-quinolin-5-yl]-acetamide

The title compound, white solid, m.p. 207° C.; MS: m/e=412.3 (M+H⁺), was prepared in accordance with the general method of example 32 from (R)—N²-indan-1-yl-quinoline-2,5-diamine (example 16) and commercially available 4-fluoro-phenyl-acetic acid.

Example 46

N-[2-((R)-Indan-1-ylamino)-quinolin-5-yl]-2-thiophen-2-yl-acetamide

The title compound, white solid, m.p. 163.5° C.; MS: m/e=400.2 (M+H⁺), was prepared in accordance with the general method of example 32 from (R)—N²-indan-1-yl-quinoline-2,5-diamine (example 16) and commercially available thiophene-2-yl-acetic acid.

Example 47

2-Imidazol-1-yl-N-[2-((R)-indan-1-ylamino)-quinolin-5-yl]-acetamide

The title compound, light brown solid, m.p. 226° C.; MS: m/e=384.3 (M+H⁺), was prepared in accordance with the general method of example 32 from (R)—N²-indan-1-yl-quinoline-2,5-diamine (example 16) and commercially available imidazol-1-yl-acetic acid.

Example 48 rac-N-[2-(5-Fluoro-indan-1-ylamino)-quinolin-5-yl]-2-(4-fluoro-phenyl)-acetamide The title compound, white solid, m.p. 187° C.; MS: m/e=430.3 (M+H⁺), was prepared in accordance with the general method of example 32 from rac-N²-(5-fluoro-indan-1-yl)-quinoline-2,5-diamine (example 37) and commercially available 4-fluoro-phenyl-acetic acid.

Example 49 rac-N-[2-(5-Fluoro-indan-1-ylamino)-quinolin-5-yl]-2-thiophen-2-yl-acetamide

The title compound, white solid, m.p. 184° C.; MS: m/e=418.0 (M+H⁺), was prepared in accordance with the general method of example 32 from rac-N²-(5-fluoro-indan-1-yl)-quinoline-2,5-diamine (example 37) and commercially available thiophene-2-yl-acetic acid.

Example 50 rac-2-(3,5-Difluoro-phenyl)-N-[2-(5-fluoro-indan-1-ylamino)-quinolin-5-yl]-acetamide The title compound, white solid, m.p. 203° C.; MS: m/e=448.3 (M+H⁺), was prepared in accordance with the general method of example 32 from rac-N²-(5-fluoro-indan-1-yl)-quinoline-2,5-diamine (example 37) and commercially available 3,5-difluoro-phenyl-acetic acid.

Example 51 rac-2-(4-Chloro-phenyl)-N-[2-(5-fluoro-indan-1-ylamino)-quinolin-5-yl]-acetamide The title compound, white solid, m.p. 221° C.; MS: m/e=446.0 (M+H⁺), was prepared in accordance with the general method of example 32 from rac-N²-(5-fluoro-indan-1-yl)-quinoline-2,5-diamine (example 37) and commercially available 4-chloro-phenyl-acetic acid.

Example 52

N-[2-((R)-Indan-1-ylamino)-quinolin-5-yl]-2-(4-methoxy-phenyl)-acetamide

The title compound, white solid, m.p. 175° C.; MS: m/e=424.3 (M+H¹), was prepared in accordance with the general method of example 32 from (R)—N²-indan-1-yl-quinoline-2,5-diamine (example 16) and commercially available 4-methoxy-phenyl-acetic acid.

Example 53 rac-N-[2-(5-Fluoro-indan-1-ylamino)-quinolin-5-yl]-2-(4-methoxy-phenyl)-acetamide The title compound, white solid, m.p. 192° C.; MS: m/e=442.3 (M+H⁺), was prepared in accordance with the general method of example 32 from rac-N²-(5-fluoro-indan-

Example 54 rac-2-(4-Fluoro-phenyl)-N-[2-(7-methoxy-indan-1-ylamino)-quinolin-5-yl]-acetamide The title compound, white solid, m.p. 195° C.; MS: m/e=442.2 (M+H⁺), was prepared in accordance with the general method of example 32 from rac-N²-(7-methoxy-indan-1-yl)-quinoline-2,5-diamine (example 19) and commercially available 4-fluoro-phenyl-acetic acid.

Example 55 rac-N-[2-(7-Methoxy-indan-1-ylamino)-quinolin-5-yl]-2-thiophen-2-yl-acetamide

The title compound, off-white solid, m.p. 194° C.; MS: m/e=430.3 (M+H⁺), was prepared in accordance with the general method of example 32 from rac-N²-(7-methoxy-indan-1-yl)-quinoline-2,5-diamine (example 19) and commercially available thiophene-2-yl-acetic acid.

Example 56 rac-2-(3,5-Difluoro-phenyl)-N-[2-(7-methoxy-indan-1-ylamino)-quinolin-5-yl]-acetamide The title compound, white solid, m.p. 248° C.; MS: m/e=460.3 (M+H⁺), was prepared in accordance with the general method of example 32 from rac-N²-(7-methoxy-indan-1-yl)-quinoline-2,5-diamine (example 19) and commercially available 3,5-difluoro-phenyl-acetic acid.

Example 57 rac-2-(4-Chloro-phenyl)-N-[2-(7-methoxy-indan-1-ylamino)-quinolin-5-yl]-acetamide The title compound, white solid, m.p. 234° C.; MS: m/e=458.3 (M+H⁺), was prepared in accordance with the general method of example 32 from rac-N²-(7-methoxy-indan-1-yl)-quinoline-2,5-diamine (example 19) and commercially available 4-chloro-phenyl-acetic acid.

Example 58 rac-N-[2-(7-Methoxy-indan-1-ylamino)-quinolin-5-yl]-2-(4-methoxy-phenyl)-acetamide The title compound, white solid, m.p. 209° C.; MS: m/e=454.2 (M+H⁺), was prepared in accordance with the general method of example 32 from rac-N²-(7-methoxy-indan-1-yl)-quinoline-2,5-diamine (example 19) and commercially available 4-methoxy-phenyl-acetic acid.

Example 59

2-(3,5-Difluoro-phenyl)-N-[2-((R)-indan-1-ylamino)-quinolin-5-yl]-acetamide

The title compound, off-white solid, M.p. 221° C.; MS: m/e=430.3 (M+H⁺), was prepared in accordance with the general method of example 32 from (R)—N²-indan-1-yl-quinoline-2,5-diamine (example 16) and commercially available 3,5-difluoro-phenyl-acetic acid.

Example 60

2-(4-Chloro-phenyl)-N-[2-((R)-indan-1-ylamino)-quinolin-5-yl]-acetamide

The title compound, white solid, m.p. 170° C.; MS: m/e=428.3 (M+H⁺), was prepared in accordance with the general method of example 32 from (R)—N²-indan-1-yl-quinoline-2,5-diamine (example 16) and commercially available 4-chloro-phenyl-acetic acid.

The invention claimed is:

1. A compound of formula (I)

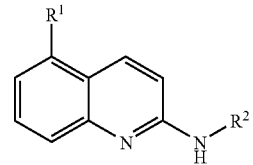

wherein
$R^1$ is alkyl, aminoalkyl, hydroxyalkyl, haloalkyl, cyanoalkyl, cycloalkyl, —C(=N—$R^i$)NR$^{ii}$R$^{iii}$, —C(=N—$R^i$)-cycloalkyl, —C(=N—$R^i$)-alkyl, —C(O)-cycloalkyl, —C(O)alkyl, heterocycloalkyl, —O-alkyl, —O-alkylene-O-alkyl, —O-alkylene-S(O)$_x$-alkyl, or —NR$^a$R$^b$;
$R^a$ and $R^b$ are each independently H, alkyl, cycloalkyl, -alkylene-S(O)$_x$-alkyl, —S(O)$_2$NR$^{iv}$R$^v$, —S(O)$_2$-alkyl, —S(O)$_2$-cycloalkyl, —C(O)-cycloalkyl, —C(O)alkyl, —C(O)-alkylene-heterocycloalkyl, —C(O)-heterocycloalkyl, —C(O)NR$^{vi}$R$^{vii}$, —C(O)-alkylene-NR$^{viii}$R$^{ix}$, —C(O)-alkylene-O-alkyl, -alkylene-NR$^{viii}$R$^{ix}$, -alkylene-O-alkyl, -alkylene-cycloalkyl, heterocycloalkyl, —C(O)—CH$_2$-phenyl, —C(O)—CH$_2$-heteroaryl;
$R^i$, $R^{ii}$, and $R^{iii}$ are each independently OH, alkoxy or H;
$R^{iv}$, $R^v$, $R^{vi}$, $R^{vii}$, $R^{viii}$ and $R^{ix}$ are each independently H, alkyl, cycloalkyl or -alkylene-N(alkyl)$_2$;
x is 0, 1 or 2, and
$R^2$ is 5- or 6-membered cycloalkyl or heterocycloalkyl, anellated with a benzo ring, wherein the benzo moiety is unsubstituted or substituted with one, two or three alkoxy, halo, alkyl or haloalkyl; and wherein
heterocycloalkyl is unsubstituted or substituted with one or more oxo, alkyl, halo, haloalkyl, haloalkoxy, alkoxy, hydroxy, hydroxyalkyl, or CN; and
phenyl and heteroaryl are each individually unsubstituted or substituted with one or more halo, alkoxy, haloalkyl, alkyl, haloalkoxy, hydroxy, or CN;
or a pharmaceutically acceptable salt thereof.

2. The compound of claim 1, wherein $R^1$ is alkyl, aminoalkyl, hydroxyalkyl, haloalkyl, cyanoalkyl, or cycloalkyl.

3. The compound of claim 2, wherein R1 is alkyl, aminoalkyl, or cycloalkyl.

4. The compound of claim 1 wherein $R^1$ is —C(=N—$R^i$)NR$^{ii}$R$^{iii}$,
—C(=N—$R^i$)-cycloalkyl, or —C(=N—$R^i$)-alkyl; and
$R^i$, $R^{ii}$ and $R^{iii}$ are each independently OH, alkoxy or H.

5. The compound of claim 4, wherein $R^1$ is —C(=N—$R^i$)NR$^{ii}$R$^{iii}$ or —C(=N—$R^i$)-cycloalkyl.

6. The compound of claim 5, wherein $R^i$, $R^{ii}$ and $R^{iii}$ are each independently H or OH.

7. The compound of claim 1, wherein $R^1$ is —C(O)-cycloalkyl, or —C(O)alkyl.

8. The compound of claim 7, wherein $R^1$ is —C(O)-cycloalkyl.

9. The compound of claim 1, wherein $R^1$ is heterocycloalkyl.

10. The compound of claim 9, wherein the heterocycloalkyl is morpholin-4-yl.

11. The compound of claim 1, wherein $R^1$ is —O-alkyl, —O-alkylene-O-alkyl, or —O-alkylene-S(O)$_x$-alkyl, wherein x is 0, 1 or 2.

12. The compound of claim 1, wherein
$R^1$ is alkyl, aminoalkyl, cycloalkyl, —C(=N—OH)NH$_2$, —C(=N—OH)-cycloalkyl, —C(O)-cycloalkyl, heterocycloalkyl, —O-alkyl, —O-alkylene-O-alkyl, —O-alkylene-S(O)$_x$-alkyl, or —NR$^a$R$^b$;
$R^a$ and $R^b$ are each independently H, alkyl, -alkylene-S(O)$_x$-alkyl, —S(O)$_2$NR$^{iv}$R$^v$, —S(O)$_2$-cycloalkyl, —C(O)-cycloalkyl, —C(O)-alkylene-heterocycloalkyl, —C(O)-heterocycloalkyl, —C(O)-alkylene-NR$^{viii}$R$^{ix}$, —C(O)-alkylene-O-alkyl, -alkylene-NR$^{viii}$R$^{ix}$, -alkylene-cycloalkyl, heterocycloalkyl, —C(O)—CH$_2$-phenyl, —C(O)—CH$_2$-heteroaryl;
$R^{iv}$, $R^v$, $R^{viii}$ and $R^{ix}$ are each independently H, alkyl, cycloalkyl or -alkylene-N(alkyl)$_2$; and
x is 0, 1 or 2.

13. The compound of claim 1 wherein $R^1$ is —NR$^a$R$^b$, wherein
$R^a$ and $R^b$ are each independently H, alkyl, cycloalkyl, -alkylene-S(O)$_x$-alkyl, —S(O)$_2$NR$^{iv}$R$^v$, —S(O)$_2$-alkyl, —S(O)$_2$-cycloalkyl, —C(O)-cycloalkyl, —C(O)alkyl, —C(O)-alkylene-heterocycloalkyl, —C(O)-heterocycloalkyl, —C(O)NR$^{vii}$R$^{vii}$, —C(O)-alkylene-NR$^{viii}$R$^{ix}$, —C(O)-alkylene-O-alkyl, -alkylene-NR$^{viii}$R$^{ix}$, -alkylene-O-alkyl, -alkylene-cycloalkyl, heterocycloalkyl, —C(O)—CH$_2$-phenyl, —C(O)—CH$_2$-heteroaryl;
$R^{iv}$, $R^v$, $R^{vi}$, $R^{vii}$, $R^{viii}$ and $R^{ix}$, are each independently H, alkyl, cycloalkyl or -alkylene-N(alkyl)$_2$; and
x is 0, 1 or 2.

14. The compound of claim 1, wherein $R^1$ is —NR$^a$R$^b$, wherein
$R^a$ and $R^b$ are each independently H, alkyl, -alkylene-S(O)$_x$-alkyl, —S(O)$_2$NR$^{iv}$R$^v$, —S(O)$_2$-alkyl, —S(O)$_2$-cycloalkyl, —C(O)-cycloalkyl, —C(O)alkyl, —C(O)-alkylene-heterocycloalkyl, —C(O)-heterocycloalkyl, —C(O)-alkylene-NR$^{viii}$R$^{ix}$, —C(O)-alkylene-O-alkyl, -alkylene-NR$^{viii}$R$^{ix}$, -alkylene-cycloalkyl, heterocycloalkyl, —C(O)—CH$_2$-phenyl, or —C(O)—CH$_2$-heteroaryl;
$R^{iv}$, $R^v$, $R^{viii}$ and $R^{ix}$ are each independently H, alkyl, cycloalkyl or -alkylene-N(alkyl)$_2$; and
x is 0, 1 or 2.

15. The compound of claim 1, wherein $R^1$ is —NR$^a$R$^b$, wherein
$R^a$ and $R^b$ are each independently
H, alkyl, -alkylene-S(O)$_x$-alkyl, —S(O)$_2$N(alkyl)$_2$, —S(O)$_2$-alkyl, —S(O)$_2$-cycloalkyl, —C(O)-cycloalkyl, —C(O)alkyl, —C(O)—CH$_2$-(4-methyl-piperazin-1-yl), —C(O)—CH$_2$-(morpholin-4-yl), —C(O)—CH$_2$-(tetrahydropyran-4-yl), —C(O)(4-methyl-piperidin-1-yl), —C(O)(1-methyl-piperidin-4-yl), —C(O)-alkylene-N(alkyl)$_2$, —C(O)-alkylene-O-alkyl, -alkylene-N(alkyl)$_2$, -alkylene-cycloalkyl, 1,1-dioxo-tetrahydrothiophen-3-yl, tetrahydropyran-4-yl, —C(O)—CH$_2$-phenyl, —C(O)—CH$_2$-(thiophen-2-yl), —C(O)—CH$_2$-(imidazol-1-yl), and
x is 0, 1 or 2; and wherein
phenyl is unsubstituted or substituted by one or two fluoro, chloro or alkoxy.

16. The compound of claim 1, wherein
$R^1$ is alkyl, aminoalkyl, cycloalkyl, —C(=N—OH)NH$_2$, —C(=N—OH)-cycloalkyl, —C(O)-cycloalkyl, heterocycloalkyl, —O-alkyl, —O-alkylene-O-alkyl, —O-alkylene-S(O)$_x$-alkyl, or —NR$^a$R$^b$;
$R^a$ and $R^b$ are each independently H, alkyl, -alkylene-S(O)$_x$-alkyl, —S(O)$_2$NR$^{iv}$R$^v$, —S(O)$_2$-cycloalkyl, —C(O)-cycloalkyl, —C(O)-alkylene-heterocycloalkyl, —C(O)-heterocycloalkyl, —C(O)-alkylene-NR$^{viii}$R$^{ix}$, —C(O)-alkylene-O-alkyl, -alkylene-NR$^{viii}$R$^{ix}$, -alkylene-cycloalkyl, heterocycloalkyl, —C(O)—CH$_2$-phenyl, —C(O)—CH$_2$-heteroaryl;
$R^{iv}$, $R^v$, $R^{viii}$ and $R^{ix}$ are each independently H, alkyl, cycloalkyl or -alkylene-N(alkyl)$_2$; and
x is 0, 1 or 2.

17. The compound of claim 1, wherein
$R^1$ is alkyl, aminoalkyl, cycloalkyl, —C(=N—R$^i$)NR$^{ii}$R$^{iii}$, —C(=N—R$^i$)-cycloalkyl, —C(O)-cycloalkyl, heterocycloalkyl, —O-alkyl, —O-alkylene-O-alkyl, —O-alkylene-S(O)$_x$-alkyl, or —NR$^a$R$^b$;
$R^a$ and $R^b$ are each independently H, alkyl, -alkylene-S(O)$_x$-alkyl, —S(O)$_2$NR$^{iv}$R$^v$, —S(O)$_2$-cycloalkyl, —C(O)-cycloalkyl, —C(O)-alkylene-heterocycloalkyl, —C(O)-heterocycloalkyl, —C(O)-alkylene-NR$^{viii}$R$^{ix}$, —C(O)-alkylene-O-alkyl, -alkylene-NR$^{viii}$R$^{ix}$, -alkylene-cycloalkyl, or heterocycloalkyl;
$R^i$ is OH;
$R^i$, $R^{ii}$, and $R^{iii}$ are each independently OH, alkoxy or H;
$R^{iv}$, $R^v$, $R^{viii}$ and $R^{ix}$, are each independently H, alkyl, cycloalkyl or -alkylene-N(alkyl)$_2$; and
x is 0, 1 or 2.

18. The compound of claim 1, wherein
$R^i$, $R^{ii}$, and $R^{iii}$ are each independently OH or H; and
$R^{iv}$, $R^v$, $R^{vi}$, $R^{vii}$, $R^{viii}$ and $R^{ix}$, are each independently H, alkyl, or cycloalkyl.

19. The compound of claim 1, wherein $R^2$ is
indan-1-yl, indan-2-yl, benzofuran-3-yl, or 1,2,3,4-tetrahydronaphthalen-1-yl, each unsubstituted or independently substituted on the benzo moiety with one, two or three alkoxy, halo, alkyl or haloalkyl.

20. The compound of claim 19, wherein the benzo moiety is substituted with one, two or three alkoxy or halo.

21. The compound of claim 20, wherein
$R^2$ is indan-1-yl, 7-methoxy-indan-1-yl, 5-fluoro-indan-1-yl, 4-methoxy-2,3-dihydro-benzofuran-3-yl, indan-2-yl, 6-methoxy-indan-1-yl, or 8-methoxy-1,2,3,4-tetrahydro-naphthalen-1-yl.

22. The compound of claim 1, selected from the group consisting of
N$^2$-(R)-Indan-1-yl-N$^5$-methyl-quinoline-2,5-diamine;
N$^5$-Cyclopropylmethyl-N$^2$-(R)-indan-1-yl-quinoline-2,5-diamine;
N$^2$-(R)-Indan-1-yl-N$^5$-(tetrahydro-pyran-4-yl)-quinoline-2,5-diamine;
(R)-Indan-1-yl-(5-morpholin-4-yl-quinolin-2-yl)-amine;
N$^2$-(R)-Indan-1-yl-N$^5$-(2-methylsulfanyl-ethyl)-quinoline-2,5-diamine;
N$^2$-(R)-Indan-1-yl-N$^5$-(2-methanesulfinyl-ethyl)-quinoline-2,5-diamine;
N$^2$-(R)-Indan-1-yl-N$^5$-(2-methanesulfonyl-ethyl)-quinoline-2,5-diamine;

N⁵-(2-Dimethylamino-ethyl)-N²-(R)-indan-1-yl-quinoline-2,5-diamine;
rac-N⁵-(1,1-Dioxo-tetrahydro-thiophen-3-yl)-N²-(6-methoxy-indan-1-yl)-quinoline-2,5-diamine; and
rac-N²-(6-Methoxy-indan-1-yl)-N⁵-(2-methylsulfanyl-ethyl)-quinoline-2,5-diamine.

23. The compound of claim 1, selected from the group consisting of
rac-N⁵-(2-Methanesulfinyl-ethyl)-N²-(6-methoxy-indan-1-yl)-quinoline-2,5-diamine;
rac-N⁵-(2-Methanesulfonyl-ethyl)-N²-(6-methoxy-indan-1-yl)-quinoline-2,5-diamine;
rac-N²-(6-Methoxy-indan-1-yl)-N⁵-(3-methylsulfanyl-propyl)-quinoline-2,5-diamine;
rac-N⁵-(3-Methanesulfonyl-propyl)-N²-(6-methoxy-indan-1-yl)-quinoline-2,5-diamine;
15: rac-N⁵-(3-Methanesulfinyl-propyl)-N²-(6-methoxy-indan-1-yl)-quinoline-2,5-diamine;
(R)—N²-Indan-1-yl-quinoline-2,5-diamine;
Cyclopropanesulfonic acid[2-((R)-indan-1-ylamino)-quinolin-5-yl]-amide;
N-[2-((R)-Indan-1-ylamino)-quinolin-5-yl]-3-methoxy-propionamide;
rac-N²-(7-Methoxy-indan-1-yl)-quinoline-2,5-diamine; and
rac-N'-{2-[(7-methoxy-indan-1-yl)amino]quinolin-5-yl}-N,N-dimethylsulfamide.

24. The compound of claim 1, selected from the group consisting of
rac-N²-(8-Methoxy-1,2,3,4-tetrahydro-naphthalen-1-yl)-quinoline-2,5-diamine;
Cyclopropanecarboxylic acid[2-((R)-indan-1-ylamino)-quinolin-5-yl]-amide;
rac-N²-Indan-2-yl-quinoline-2,5-diamine;
(R)-Indan-1-yl-[5-(2-methoxy-ethoxy)-quinolin-2-yl]-amine;
(R)-Indan-1-yl-(5-methoxy-quinolin-2-yl)-amine;
(R)-Indan-1-yl-[5-(2-methylsulfanyl-ethoxy)-quinolin-2-yl]-amine;
(R)-Indan-1-yl-[5-(2-methanesulfonyl-ethoxy)-quinolin-2-yl]-amine;
N-Hydroxy-2-((R)-indan-1-ylamino)-quinoline-5-carboxamidine;
(5-Aminomethyl-quinolin-2-yl)-(R)-indan-1-yl-amine; and
Cyclopropyl-[2-((R)-indan-1-ylamino)-quinolin-5-yl]-methanone.

25. The compound of claim 1, selected from the group consisting of
Cyclopropyl-[2-((R)-indan-1-ylamino)-quinolin-5-yl]-methanone oxime;
2-Dimethylamino-N-[2-((R)-indan-1-ylamino)-quinolin-5-yl]-acetamide;
N-[2-((R)-Indan-1-ylamino)-quinolin-5-yl]-2-morpholin-4-yl-acetamide;
1-Methyl-piperidine-4-carboxylic acid[2-((R)-indan-1-ylamino)-quinolin-5-yl]-amide;
N-[2-((R)-Indan-1-ylamino)-quinolin-5-yl]-2-(tetrahydro-pyran-4-yl)-acetamide;
4-Methyl-piperazine-1-carboxylic acid[2-((R)-indan-1-ylamino)-quinolin-5-yl]-amide;
rac-N²-[5-Fluoro-indan-1-yl]-quinoline-2,5-diamine;
2-Dimethylamino-N-[2-(5-(RS)-fluoro-indan-1-ylamino)-quinolin-5-yl]-acetamide;
rac-N²-(4-Methoxy-2,3-dihydro-benzo furan-3-yl)-N⁵-(2-methylsulfanyl-ethyl)-quinoline-2,5-diamine; and
N⁵-(2-Methanesulfonyl-ethyl)-N²-(RS)-(4-methoxy-2,3-dihydro-benzofuran-3-yl)-quinoline-2,5-diamine.

26. The compound of claim 1, selected from the group consisting of
rac-N²-(4-Methoxy-2,3-dihydro-benzofuran-3-yl)-N⁵-(tetrahydro-pyran-4-yl)-quinoline-2,5-diamine;
N-[2-(RS)-(7-Methoxy-indan-1-ylamino)-quinolin-5-yl]-2-(4-methyl-piperazin-1-yl)-acetamide;
N-[2-((S)-Indan-1-ylamino)-quinolin-5-yl]-2-(4-methyl-piperazin-1-yl)-acetamide;
(5-Cyclopropyl-quinolin-2-yl)-(R)-indan-1-yl-amine;
2-(4-Fluoro-phenyl)-N-[2-((R)-indan-1-ylamino)-quinolin-5-yl]-acetamide;
N-[2-((R)-Indan-1-ylamino)-quinolin-5-yl]-2-thiophen-2-yl-acetamide;
2-Imidazol-1-yl-N-[2-((R)-indan-1-ylamino)-quinolin-5-yl]-acetamide;
rac-N-[2-(5-Fluoro-indan-1-ylamino)-quinolin-5-yl]-2-(4-fluoro-phenyl)-acetamide;
rac-N-[2-(5-Fluoro-indan-1-ylamino)-quinolin-5-yl]-2-thiophen-2-yl-acetamide; and
rac-2-(3,5-Difluoro-phenyl)-N-[2-(5-fluoro-indan-1-ylamino)-quinolin-5-yl]-acetamide.

27. The compound of claim 1, selected from the group consisting of
rac-2-(4-Chloro-phenyl)-N-[2-(5-fluoro-indan-1-ylamino)-quinolin-5-yl]-acetamide;
N-[2-((R)-Indan-1-ylamino)-quinolin-5-yl]-2-(4-methoxy-phenyl)-acetamide;
rac-N-[2-(5-Fluoro-indan-1-ylamino)-quinolin-5-yl]-2-(4-methoxy-phenyl)-acetamide;
rac-2-(4-Fluoro-phenyl)-N-[2-(7-methoxy-indan-1-ylamino)-quinolin-5-yl]-acetamide;
rac-N-[2-(7-Methoxy-indan-1-ylamino)-quinolin-5-yl]-2-thiophen-2-yl-acetamide;
rac-2-(3,5-Difluoro-phenyl)-N-[2-(7-methoxy-indan-1-ylamino)-quinolin-5-yl]-acetamide;
rac-2-(4-Chloro-phenyl)-N-[2-(7-methoxy-indan-1-ylamino)-quinolin-5-yl]-acetamide;
rac-N-[2-(7-Methoxy-indan-1-ylamino)-quinolin-5-yl]-2-(4-methoxy-phenyl)-acetamide;
2-(3,5-Difluoro-phenyl)-N-[2-((R)-indan-1-ylamino)-quinolin-5-yl]-acetamide; and
2-(4-Chloro-phenyl)-N-[2-((R)-indan-1-ylamino)-quinolin-5-yl]-acetamide.

28. A pharmaceutical composition comprising a therapeutically effective amount of a compound of formula I

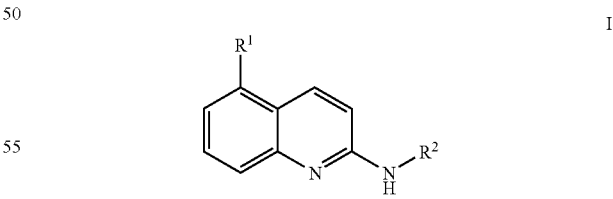

wherein
R¹ is alkyl, aminoalkyl, hydroxyalkyl, haloalkyl, cyanoalkyl, cycloalkyl, —C(=N—Rⁱ)NRⁱⁱRⁱⁱⁱ, —C(=N—Rⁱ)-cycloalkyl, —C(=N—Rⁱ)-alkyl, —C(O)-cycloalkyl, —C(O)alkyl, heterocycloalkyl, —O-alkyl, —O-alkylene-O-alkyl, —O-alkylene-S(O)ₓ-alkyl, or —NRᵃRᵇ;
Rᵃ and Rᵇ are each independently H, alkyl, cycloalkyl, -alkylene-S(O)ₓ-alkyl, —S(O)₂NRⁱᵛRᵛ, —S(O)₂-alkyl, —S(O)$_2$-cycloalkyl, —C(O)-cycloalkyl, —C(O)alkyl, —C(O)-alkylene-heterocycloalkyl, —C(O)-heterocycloalkyl, —C(O)NR$^{vi}$R$^{vii}$, —C(O)-alkylene-NR$^{viii}$R$^{ix}$, —C(O)-alkylene-O-alkyl, -alkylene-NR$^{viii}$R$^{ix}$, -alkylene-O-alkyl, -alkylene-cycloalkyl, heterocycloalkyl, —C(O)—CH$_2$-phenyl, —C(O)—CH$_2$-heteroaryl;

R$^i$, R$^{ii}$, and R$^{iii}$ are each independently OH, alkoxy or H;

R$^{iv}$, R$^v$, R$^{vi}$, R$^{vii}$, R$^{viii}$ and R$^{ix}$ are each independently H, alkyl, cycloalkyl or -alkylene-N(alkyl)$_2$;

x is 0, 1 or 2, and

R$^2$ is 5- or 6-membered cycloalkyl or heterocycloalkyl, anellated with a benzo ring, wherein the benzo moiety is unsubtituted or substituted with one, two or three alkoxy, halo, alkyl or haloalkyl; and wherein heterocycloalkyl is unsubstituted or substituted with one or more oxo, alkyl, halo, haloalkyl, haloalkoxy, alkoxy, hydroxy, hydroxyalkyl, or CN; and phenyl and heteroaryl are each individually unsubstituted or substituted with one or more halo, alkoxy, haloalkyl, alkyl, haloalkoxy, hydroxy, or CN;

or a pharmaceutically acceptable salt thereof and a pharmaceutically acceptable carrier.

* * * * *